US012678501B2

(12) United States Patent
Boire et al.

(10) Patent No.: US 12,678,501 B2
(45) Date of Patent: Jul. 14, 2026

(54) MODULATING PERMEABILITY OF THE BLOOD CEREBROSPINAL FLUID BARRIER

(71) Applicant: MEMORIAL SLOAN-KETTERING CANCER CENTER, New York, NY (US)

(72) Inventors: Adrienne Boire, New York, NY (US); Joan Massague, New York, NY (US)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 92 days.

(21) Appl. No.: 17/667,083

(22) Filed: Feb. 8, 2022

(65) Prior Publication Data

US 2022/0152205 A1 May 19, 2022

Related U.S. Application Data

(60) Division of application No. 15/984,087, filed on May 18, 2018, now Pat. No. 11,305,014, which is a (Continued)

(51) Int. Cl.

| | |
|---|---|
| ***A61K 45/00*** | (2006.01) |
| ***A61K 31/166*** | (2006.01) |
| ***A61K 31/4745*** | (2006.01) |
| ***A61K 31/7068*** | (2006.01) |
| ***A61K 31/7105*** | (2006.01) |
| ***A61K 45/06*** | (2006.01) |

(Continued)

(52) U.S. Cl.

CPC ............ *A61K 45/00* (2013.01); *A61K 31/166* (2013.01); *A61K 31/4745* (2013.01); *A61K 31/7068* (2013.01); *A61K 31/7105* (2013.01); *A61P 35/04* (2018.01); *G01N 33/57557* (2026.01); *A61K 45/06* (2013.01)

(58) Field of Classification Search

None

See application file for complete search history.

(56) References Cited

U.S. PATENT DOCUMENTS

| | | | | |
|---|---|---|---|---|
| 6,489,128 | B1 | 12/2002 | Lim et al. | |
| 2007/0054325 | A1 * | 3/2007 | Pekny ................ | G01N 33/6893 435/7.2 |

(Continued)

FOREIGN PATENT DOCUMENTS

| | | | |
|---|---|---|---|
| EP | 2 212 699 | A1 | 8/2010 |
| WO | WO 2009/066258 | A1 | 5/2009 |
| WO | WO 2009/149306 | A2 | 12/2009 |

OTHER PUBLICATIONS

Koopmans et al. BBA Clinical, vol. 1, 2014, pp. 44-51, ISSN 2214-6474 (Year: 2014).*

(Continued)

*Primary Examiner* — Jeffrey S Lundgren
*Assistant Examiner* — Anthony Joseph Seitz
(74) *Attorney, Agent, or Firm* — Baker Botts L.L.P.

(57) ABSTRACT

The present invention relates to methods and compositions for modulating the blood CSF barrier and for diagnosing, preventing and/or treating leptomeningeal metastasis. In particular embodiments of the invention, the permeability of the blood CSF barrier is modulated by agonists or antagonists of Complement Component 3 (C3) or its receptor.

20 Claims, 17 Drawing Sheets

Figure 1:
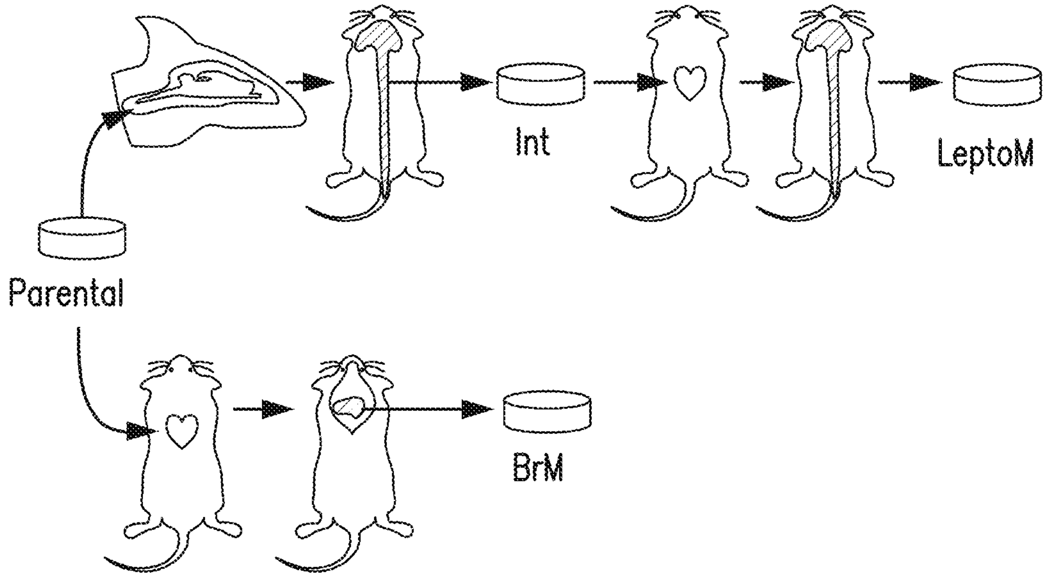

Related U.S. Application Data continuation of application No. PCT/US2016/062880, filed on Nov. 18, 2016.

(60) Provisional application No. 62/258,044, filed on Nov. 20, 2015.

(51) Int. Cl.

| | |
|---|---|
| ***A61P 35/04*** | (2006.01) |
| ***G01N 33/575*** | (2026.01) |

(56) References Cited

U.S. PATENT DOCUMENTS

| | | | |
|---|---|---|---|
| 2011/0135656 | A1 | 6/2011 | Medof et al. |
| 2012/0171118 | A1 | 7/2012 | Papisov |
| 2013/0095518 | A1 | 4/2013 | Akagi et al. |
| 2014/0011274 | A1 | 1/2014 | Clarke et al. |
| 2014/0219999 | A1 | 8/2014 | Lambris et al. |

OTHER PUBLICATIONS

Sayah et al., Molecular Brain Research, vol. 112, Issues 1-2, 2003, pp. 53-60, Issn 0169-328X (Year: 2003).*
Shin et al., (2012) Expert Opinion on Pharmacotherapy, 13:15, 2189-2206 (Year: 2012).*
Alibek et al., Infect Agents Cancer 7, 33 (2012) (Year: 2012).*
Mook-Kanamori et al., 2011. Pathogenesis and Pathophysiology of Pneumococcal Meningitis. Clin Microbiol Rev 24 (Year: 2011).*
Denonne et al., Bioorganic & Medicinal Chemistry Letters, vol. 17, Issue 12, 2007, pp. 3262-3265, ISSN 0960-894X (Year: 2007).*
Ling et al., Brain-Derived Neurotrophic Factor Rescues Neurons From Bacterial Meningitis, Pediatric Neurology, vol. 36, Issue 5, 2007, pp. 324-329 (Year: 2007).*
Denonne et al., Discovery of new C3aR ligands. Part 1: Arginine derivatives, Bioorganic & Medicinal Chemistry Letters, vol. 17, Issue 12, 2007, pp. 3258-3261 (Year: 2007).*
U.S. Appl. No. 15/984,087, (US 2018/0334508), filed May 18, 2018 (Nov. 22, 2018).
"Difficult Case Analysis," Weihal Wu, et al., p. 242, Hebei Science and Technology Press (Nov. 30, 2014) [see English translation of Office Action mailed Jul. 22, 2021 in Chinese Application No. 201680079549.1].
Altundag et al., "Clinicopathologic Characteristics and Prognostic Factors in 420 Metastatic Breast Cancer Patients with Central Nervous System Metastasis," Cancer 110(12):2640-2647 (2007).
Ames et al., "Identification of a Selective Nonpeptide Antagonist of the Anaphylatoxin C3a Receptor That Demonstrates Antiinflammatory Activity in Animal Models," J. Immunol. 166:6341-6348 (2001).
Arumugam et al., "Neuroprotection in Stroke by Complement Inhibition and Immunoglobulin Therapy," Neuroscience, 158(3):1074-1089 (2009).
Bos et al., "Genes that mediate breast cancer metastasis to the brain," Nature 459(7249):1005-1009 (2009).
Brower et al., "Management of leptomeningeal metastases: Prognostic factors and associated outcomes," J. Clin. Neurosci. 27:130-137 (2016).
Chiang et al., "Molecular Basis of Metastasis," N Engl J Med 359(26):2814-2823 (2008).
Clarke et al., "Leptomeningeal metastases in the MRI era," Neurology 74:1449-1454 (2010).
Day et al., "The fluorescent protein palette: tools for cellular imaging," Chem. Soc. Rev. 38(10):2887-2921 (2009).
DeAngelis et al., "Leptomeningeal Metastasis," Cancer Invest 23(2):145-154 (2005).
DeAngelis et al., Chapter 7: Leptomeningeal Metastases in Neurologic Complications of Cancer, Second ed. Oxford: Oxford University Press; pp. 240-281 (2008).
Extended European Search Report dated Sep. 6, 2019 in EP Application No. 16867272.
Fidler, "Selection of Successive Tumour Lines for Metastasis," Nature: New Biology 242:148-149 (1973).
International Search Report mailed Apr. 12, 2017 in International Application No. PCT/US16/62880.
Jacob et al., "Metastatic Competence Can Emerge with Selection of Preexisting Oncogenic Alleles without a Need of New Mutations," Cancer Research 75(18):3713-3719 (2015).
Kang et al., "A multigenic program mediating breast cancer metastasis to bone," Cancer Cell 3:537-549 (2003).
Kang et al., "Breast cancer bone metastasis mediated by the Smad tumor suppressor pathway," PNAS 102(39):13909-13914 (2005).
Kesari et al., "Leptomeningeal metastases," Neurol. Clin. 21(1):25-66 (2003).
Le Rhun et al., "Carcinomatous meningitis: Leptomeningeal metastases in solid tumors," Surgical Neurology International 4:S265-88 (2013).
Lim et al., "C5aR and C3aR antagonists each inhibit diet-induced obesity, metabolic dysfunction, and adipocyte and macrophage signaling," The FASEB Journal, 27(2):822-831 (2013).
Massague et al., "Metastatic Colonization," Nature 529(7586):298-306 (2016).
Minn et al., "Distinct organ-specific metastatic potential of individual breast cancer cells and primary tumors," The Journal of Clinical Investigation 115(1):44-55 (2005).
Minn et al., "Genes that mediate breast cancer metastasis to lung," Nature 436(7050):518-524 (2005).
Office Action mailed Jul. 22, 2021 in Chinese Application No. 201680079549.1 [English translation].
Olson et al., "Infiltration of the Leptomeninges by Systemic Cancer," Archives of Neurology 30(2):122-137 (1974).
Posner et al., "Intracranial Metastases from Systemic Cancer," Advances in Neurology 19:579-592 (1978).
Quail et al., "Microenvironmental regulation of tumor progression and metastasis," Nat. Med. 19(11):1423-1437 (2013).
Reijneveld et al., "A simple mouse model for leptomeningeal metastases and repeated intrathecal therapy," Journal of Neuro-Oncology 42:137-142 (1999).
Rynkowski et al., "C3a receptor antagonist attenuates brain injury after intracerebral hemorrhage," J Cerebral Blood Flow Metabolism 29(1):98-107 (2009).
Scott et al., "Leptomeningeal metastases in breast cancer," Am J. Cancer Res 3(2):117-126 (2013).
Scully et al., "Selective Hexapeptide Agonists and Antagonists for Human Complement C3a Receptor," 2010, Journal of Medicinal Chemistry, 53(13), pp. 4938-4948. (2010).
Spector et al., "A balanced view of the cerebrospinal fluid composition and functions: Focus on adult humans," Experimental Neurology 273:57-68 (2015).
Supplemental Partial European Search Report dated Jun. 4, 2019 in Application No. EP 16867272.
Valiente et al., "Serpins Promote Cancer Cell Survival and Vascular Co-Option in Brain Metastasis," Cell 156(5):1002-1016 (2014).
Waki et al., "Prognostic factors and clinical outcomes in patients with leptomeningeal metastasis from solid tumors," J. Neurooncol. 93:205-212 (2009).
Wasserstrom et al. "Diagnosis and Treatment of Leptomeningeal Metastases From Solid Tumors: Experience with 90 Patients," Cancer 49:759-772 (1982).
Zhang et al., "Transforming Growth Factor-132 is a Molecular Determinant for Site-specific Melanoma Metastasis in the Brain," Cancer Research 69(3):828-835 (2009).
Zuo et al., "Protective Effects of Ephedra Sinica Extract on Blood-Brain Barrier Integrity and Neurological Function Correlate with Complement C3 Reduction After Subarachnoid hemorrhage in Rats," Neuroscience Letters, 609:216-222 (2015).

* cited by examiner

FIGURE 3A
| Cell Line | Primary | Suptype | Mouse |
|---|---|---|---|
| MDA231 | Human Breast Cancer | ER(−)/PR(−)/Her2(−) | Nu/nu |
| HCC1954 | Human Breast Cancer | ER(−)/PR(−)/Her2(+) | Nu/nu |
| Lewis Lung Carcinoma | Mouse Lung Cancer | Non-small cell | C57/Bl6 |
| PC9 | Human Lunch Cancer | EGFR | Nu/nu |
FIGURE 3B
MDA231 human breast carcinoma
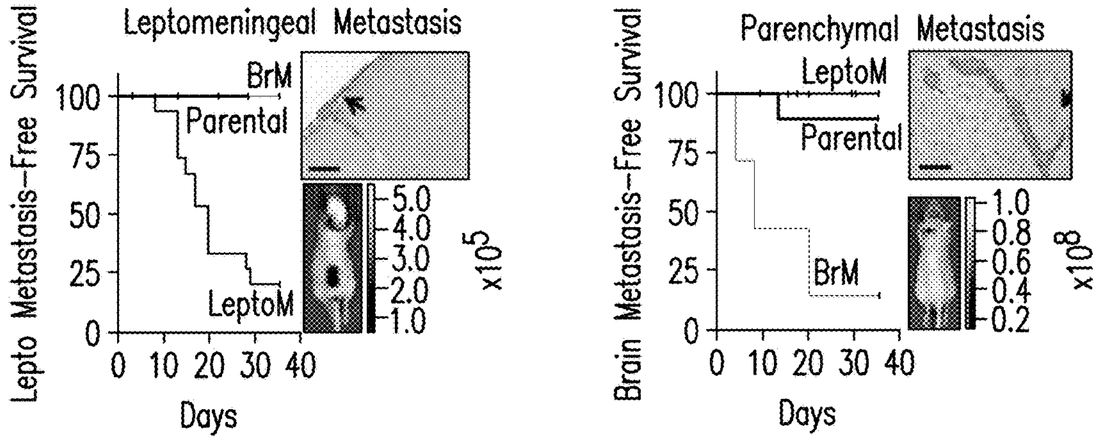
FIGURE 3C
PC9 human lung carcinoma
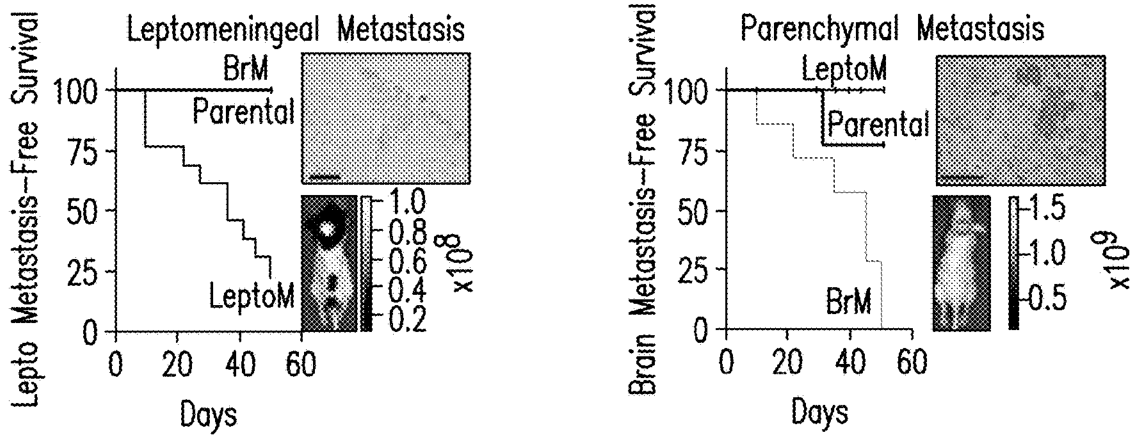

MODULATING PERMEABILITY OF THE BLOOD CEREBROSPINAL FLUID BARRIER

PRIORITY CLAIM

This application is a divisional of U.S. patent application Ser. No. 15/984,087, filed May 18, 2018, which is a continuation of International Patent Application No. PCT/US2016/062880, filed Nov. 18, 2016, which claims priority to U.S. Provisional Application No. 62/258,044, filed Nov. 20, 2015, the contents of all of which are hereby incorporated by reference in their entireties.

1. INTRODUCTION

The present invention relates to methods and compositions for modulating the blood/cerebrospinal fluid barrier ("B-CSF-B") and for diagnosing, preventing and treating leptomeningeal metastasis and/or infectious disease.

2. BACKGROUND OF THE INVENTION

The leptomeninges surround the brain and spinal cord and contain the cerebrospinal fluid (CSF). Cancer spread into the CSF compartment, termed leptomeningeal metastasis, presents a formidable clinical challenge. Metastases to this fluid-filled space disseminate rapidly throughout the central nervous system, settling on and invading the brain, spinal cord, cranial and spinal nerves, resulting in rapid neurologic disability and death. Untreated, patients succumb to leptomeningeal tumor burden 6-8 weeks after diagnosis (20, 7); current treatments offer little improvement on this grim prognosis (21, 22). Although any systemic cancer may seed the leptomeninges, the majority of leptomeningeal metastases from solid malignancy arise from primary breast and lung cancers (22). Approximately 5-10% of patients with solid tumors harbor leptomeningeal metastasis, and this number is expected to rise (23, 25). The molecular basis of this morbid, increasingly prevalent complication of cancer remains unknown.

The choroid plexus is a polarized secretory epithelium that resides within the ventricles, secretes CSF and restricts entry of cells and plasma components into the leptomeningeal space. Within the leptomeningeal space, metastatic outgrowth occurs in suspension, as well as in contact with the pia matter, a thin mesenchymal tissue layer. Once established, leptomeningeal metastases may invade the parenchyma and coat the entire neuro-axis, including the spinal cord and roots.

The CSF is acellular and poor in protein, glucose and cytokine content (18). This composition makes the leptomeningeal space markedly different as a metastasis microenvironment compared to the parenchyma of other major metastasis organ sites such as the brain, bone marrow, liver, or lungs. The stromal components of these other sites, including mesenchymal, immune, and epithelial cells, the vasculature, extracellular matrix structures, and local and systemic signals, provide sources of support for metastatic outgrowth, and much has been learned about the cellular and molecular determinants of metastasis at these sites (24, 26). By contrast, very little is known about how cancer cells that infiltrate the leptomeningeal space can proliferate in the compositionally simple context of the CSF.

3. SUMMARY OF THE INVENTION

The present invention relates to methods and compositions for modulating the blood/cerebrospinal fluid barrier ("B-CSF-B") and for diagnosing, preventing and/or treating leptomeningeal metastasis (also known as carcinomatous meningitis or leptomeningeal carcinomatosis). It is based, at least in part, on the discovery of a distinct set of genes—a gene "signature"—differentially expressed by cells competent to seed and grow within the leptomeninges. One non-limiting example of a gene in that "signature" set is complement component 3 ("C3" or "$C_3$").

Certain non-limiting embodiments of the invention are based, at least in part, on the discoveries that (i) circulating cancer cells produce complement C3; (ii) C3 is detectable in CSF from patients with cytology- or MRI-proven leptomeningeal metastasis; (iii) agonists of C3 or its receptor C3aR (alternatively designated as $C_3$aR) increase permeability of the blood-CSF-barrier to cancer cells and other agents; and (iv) antagonists of C3 or C3aR decrease permeability of the blood-CSF-barrier to cancer cells and other agents, and inhibits growth of cancer cells within this space.

Thus, the invention manipulates the B-CSF-B itself, and is therefore applicable to a wide range of meningeal pathologies and conditions involving the central nervous system. Forcing closure of the B-CSF-B can reduce cancer cell access to and/or survival within the meninges. Conversely, opening the B-CSF-B can improve entry of systemic chemotherapy into the CSF. In the case of infectious meningitis, opening the B-CSF-B may improve penetration of antimicrobials into the CSF.

Accordingly, in certain embodiments, the present invention provides for a method of increasing permeability of the B-CSF-B in a subject in need of such treatment comprising administering, to the subject, an effective amount of an agonist of C3 or C3aR; where, for example and not by way of limitation, the subject may be suffering from a condition that would benefit from the presence of a therapeutic or diagnostic agent in the CSF. Examples of such conditions include, but are not limited to, an infectious disease of the central nervous system, including but not limited to bacterial, viral, fungal, protozoan, or parasitic (e.g., helminthic) infection, including but not limited to meningitis; a malignant disease of the central nervous system, including but not limited to breast cancer, lung cancer, or melanoma, including but not limited to leptomeningeal meningitis; a degenerative disease of the nervous system, such as, but not limited to, Alzheimer's disease, Parkinson's Disease, Huntington's Chorea, or Pick's Disease; cerebrovascular disease; and/or acute damage to the CNS, for example by cerebrovascular accident, surgery, or trauma. In various embodiments, the invention provides methods of treating these conditions by administering an effective amount of an agonist of C3 or C3aR.

In certain further embodiments, the present invention provides for a method of decreasing permeability of the B-CSF-B in a subject in need of such treatment comprising administering, to the subject, an effective amount of an antagonist of C3 or C3aR; where, for example and not by way of limitation, the subject may (i) be suffering from a malignant disease, and may therefore be at risk of cancer cells penetrating the B-CSF-B barrier; (ii) have findings consistent with the existence of leptomeningeal disease; (iii) be suffering from breast cancer, lung cancer, or melanoma; and/or (v) be suffering from a metabolic disease or a disease mediated by a toxin.

In certain further embodiments, the present invention provides for a method of diagnosing leptomeningeal metastasis in a subject, comprising determining that the level of C3 in the CSF of the subject is elevated relative to the level in the CSF of a healthy control subject. In related non-limiting embodiments, the invention provides for a kit for practicing said method, said kit comprising a means for detecting C3 such as but not limited to an anti-C3 antibody or antibody fragment or single chain antibody, and, optionally, instructions or access to instructions for use of the kit and its use in determining C3 levels in the CSF and its association with leptomeningeal metastatic disease; a secondary antibody and/or detection agent, and/or materials for performing a lumbar puncture or reservoir tap. Said kit may further comprise an antibody suitable for detecting a breast cancer, lung cancer, or melanoma cell in the CSF. Said kit may further comprise a means for determining the level of glucose in the CSF.

In certain further embodiments, the present invention provides for a method of treating a subject having or suspected of having a cancer, comprising treating the subject with a C3 or C3aR antagonist and/or a C3 or C3aR antagonist together with a second therapeutic agent. For example, and not by way of limitation, the invention provides for a method of treating a subject having or suspected of having a cancer, comprising diagnosing leptomeningeal metastasis in a subject by determining that the level of C3 in the CSF of the subject is elevated relative to the level in the CSF of a healthy control subject and then treating the subject with a C3 or C3aR antagonist and/or a C3 or C3aR antagonist together with a second therapeutic agent.

In certain further embodiments, the present invention provides for a model system for leptomeningeal metastasis comprising a model animal inoculated with leptomeningeal metastatic cells prepared by a method comprising inoculating, into a subarachnoid space of a first generator animal, parental cancer cells and then, after a period of time, collecting cancer cells from the meninges of the first generator animal and inoculating said collected cells into a subarachnoid space of a second generator animal and then, after a period of time, collecting cancer cells from the meninges of the second generator animal, optionally repeating said selection step one or more times, to obtain a population of leptomeningeal metastatic cells ("Int" cells) to be used to produce the model animal. In certain non-limiting embodiments said population of leptomeningeal metastatic cells may be further injected into the systemic circulation of a host animal, and then, after a period of time, cancer cells may be collected from the meninges of the host animal, termed "LeptoM" cells. An animal having detectable LeptoM cells in its meninges is a model system according to the invention (including the host animal, post-inoculation with Int cells and establishment of meningeal growth). In non-limiting embodiments, the model animal and/or generator animal may be a non-human animal such as, but not limited to, a non-human primate, a mouse, a rat, a hamster, a rabbit, a guinea pig, a dog, a cat, a horse, a cow, a pig, or a sheep.

4. BRIEF DESCRIPTION OF THE FIGURES

FIG. 1. Schematic showing methodology for developing a mouse model of leptomeningeal metastasis. Cells express a bioluminescent marker (luciferase) and can be detected by bioluminescent imaging ("BLI"). Parental Cells, expressing luciferin and GFP are injected into the cisterna magna. Tumor growth is monitored by bioluminescent imaging (BLI). Cells are collected from the basilar meninges and maintained in culture. This is repeated three times to create "Int" cells. Then, Int cells are injected intracardially, and tumor burden is monitored by BLI. Cells are collected as before and designated "LeptoM." Parental Cells injected intracardially that go on to form brain metastasis are designated "BrM" cells.

Figure 2A:
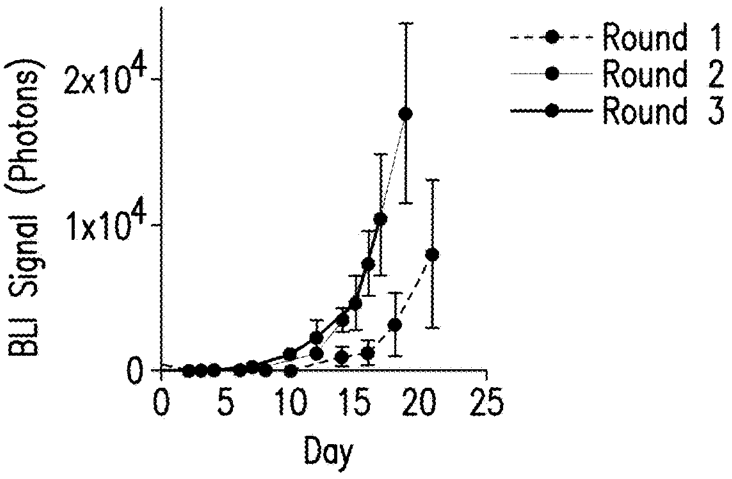
Figure 2B:
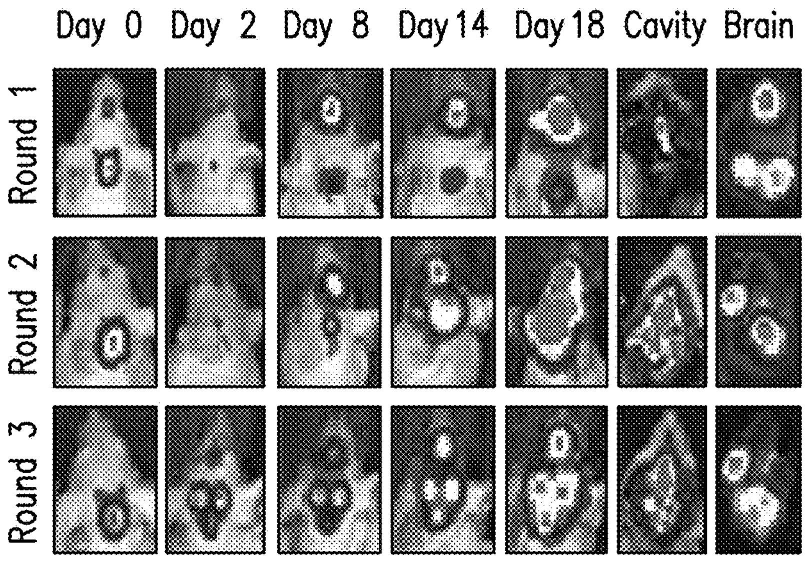
Figure 2C:
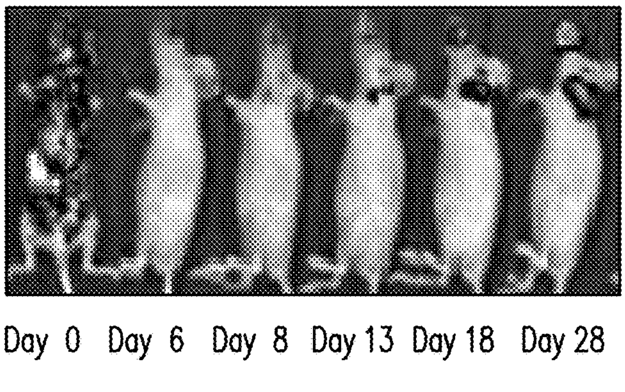

FIG. 2A-2C. Validation of mouse model of leptomeningeal metastasis: MDA231 model. (A) $2\times10^4$ parental cells, expressing luciferin and GFP, injected into the cisterna magna, monitored over time by BLI, each successive round of in vivo selection is shown. (B) Representative BLI images of mice harboring leptomeningeal tumor cells over time. Post-mortem BLI of basilar meninges and brain are shown as "Cavity" and "Brain" respectively. (C) Representative mouse after intracardiac injection of $5\times10^4$ Int cells demonstrating accumulation of cells in leptomeningeal space.

FIG. 3A-3E. Mouse models of leptomeningeal metastasis are phenotypically distinct from models of parenchymal metastasis. (A) Characteristics of parental cell lines. (B)-(E) $5\times10^4$ Parental, BrM or LeptoM cells were injected intracardially into recipient mice, tumor growth was monitored by BLI, final intracranial localization was determined by histopathology. Metastasis free-survival, representative histopathology and BLI are shown for each model system.

Figure 4:
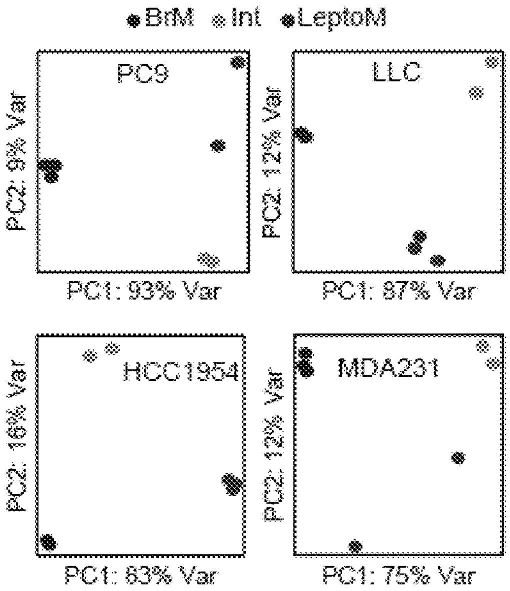

FIG. 4. Mouse models of leptomeningeal metastasis are transcriptomally distinct from models of parenchymal metastasis. For each model system, RNASeq was performed with BrM, (three technical replicates each), Int (two biological replicates each) and LeptoM (three biological replicates each) cells. Genes with fold change >2 or <0.05, base mean>50, p<0.05 were collected for further analysis. Principle component analysis is pictured.

Figure 5A:
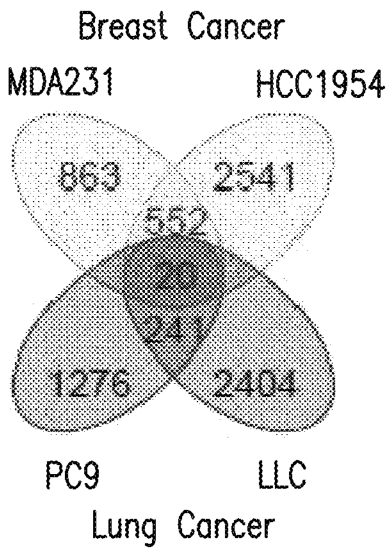
Figure 5B:
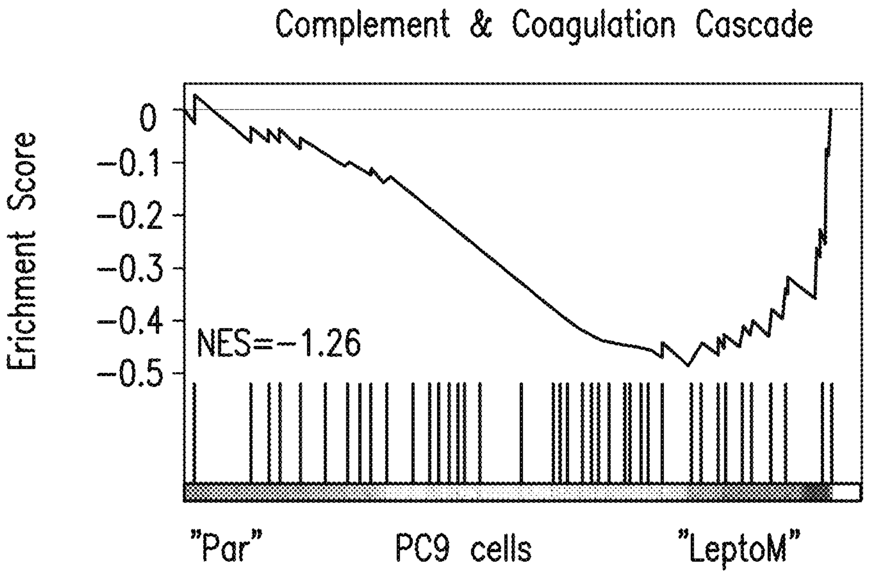
Figure 5C:
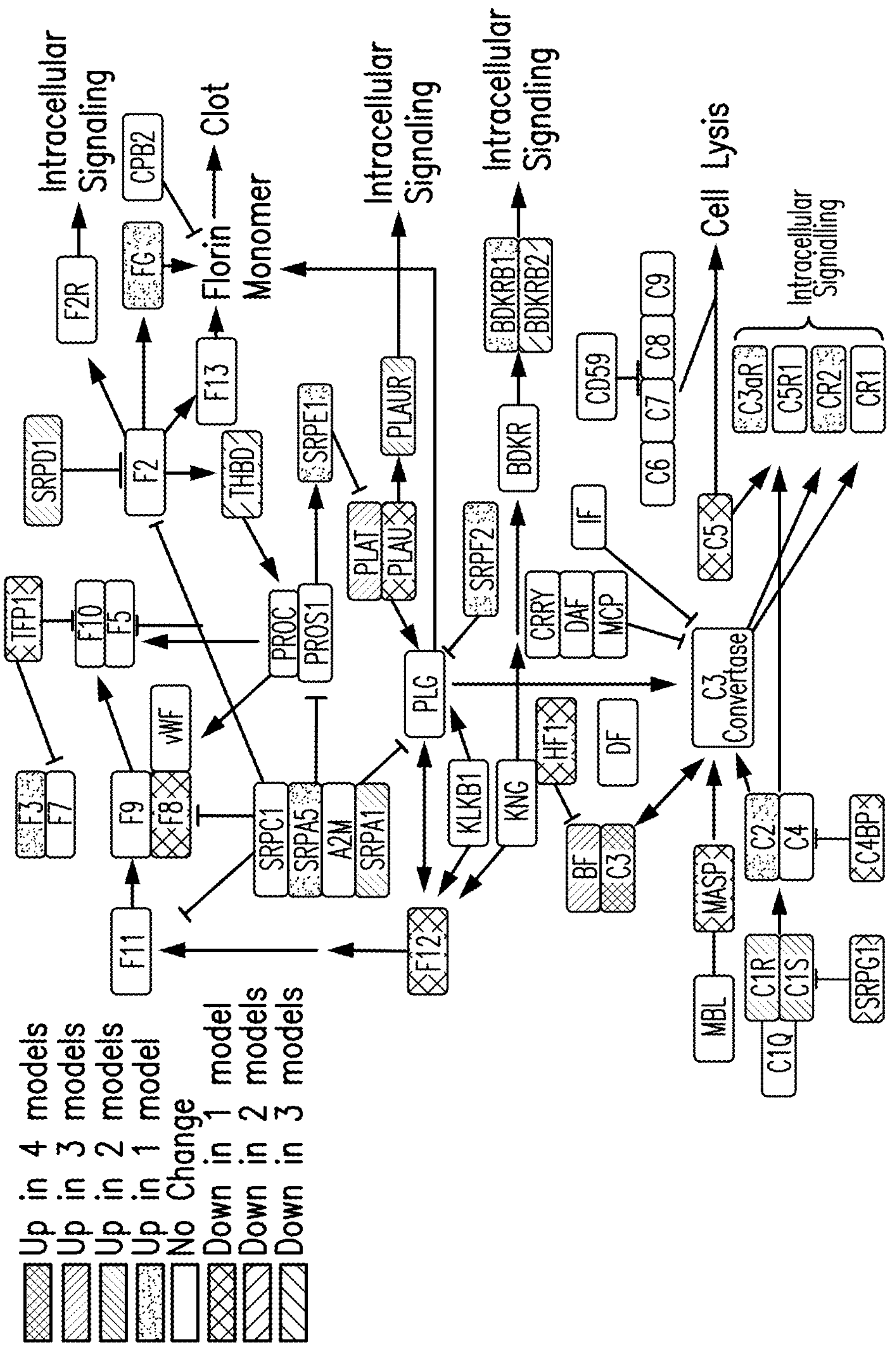

FIG. 5A-5C. Complement C3 is upregulated in mouse models of leptomeningeal metastasis. RNASeq was undertaken as described in FIG. 4. (A) Differentially expressed genes from each model system in common are plotted in the Venn diagram. 552 are shared by MDA231 and HCC1954; 241 are shared by PC9 and LLC; and 20 are shared by all four. (B) Gene ontology analysis of differentially expressed genes by DAVID pathway analysis reveals upregulation of complement and coagulation cascades. Representative analysis of PC9 model is shown. (C) Differential expression of genes in all models is plotted on a diagram of the complement and coagulation cascades.

FIG. 6A-6D. Validation of the C3 gene. (A)-(C) PC9, LLC and MDA231-LeptoM cells expressing short hairpins against C3 were injected intracisternally into recipient mice; tumor growth was monitored by BLI. (D) LLC-LeptoM cells were injected intracisternally into recipient mice with C3 wt (+/+) or C3 knock-out (−/−) genetic background; tumor growth was monitored by BLI.

FIG. 7A-7F. C3aR activation alters B-CSF-barrier integrity. (A) Immunofluorescence of mouse choroid plexus for C3aR (red) and the apically expressed SPAK (green). (B) Trans-epithelial resistance in response to C3a in an in vitro model of B-CSF-B employing human choroid plexus epithelial cells (HuCPEpi). (C) Conditioned medium from MDA231 Parental cells (green) supplemented with recombinant mouse C3a (open circles) or vehicle (closed circles) was used to treat the monolayer prior to TEER measurements. (D) Conditioned medium from MDA231 LeptoM cells was not treated with antibody (closed circle), or immunodepleted with anti-C3 (open circles) or IgG control (black squares) prior to TEER measurements. (E) Mice ($C3aR^{+/+}$ or $^{-/-}$) were parenterally pretreated with recombinant mouse C3a or vehicle prior to intracardiac infusion of mixed fluorescently labeled dextrans. 30 minutes later, CSF and blood were sampled and analyzed by fluorimetry. In the bar graphs, for each dextran size, fluorescence in animals treated with rmC3a is represented by the bar on the right (vehicle represented by the bar on the left). (F) Mouse choroid plexus treated with C3a or vehicle for 2 hours prior to fixation and staining for ZO-1 and Claudin.

FIG. 8A-8E. Clinical Validation. (A) C3 measured by ELISA from cerebrospinal fluid obtained from patients suspected of leptomeningeal metastasis n=69 samples. (B) Immunohistochemistry of primary tumors from patients with suspected leptomeningeal metastasis. Representative images are shown of C3 low and high staining lesions n=31 samples. (C) Clinical outcome is presented as survival curve. Immunohistochemistry of primary and brain metastasis for C3. Unmatched (D) and matched (E) paired samples are presented.

Figure 9:
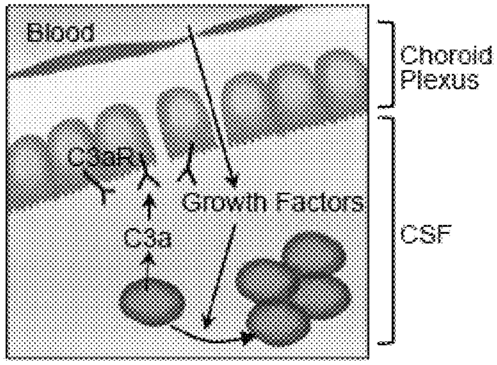

FIG. 9. Complement C3 produced by cancer cells reduced integrity of the Blood-CSF-barrier, allowing for passage of plasma contents into the CSF, creating a more hospitable environment for metastatic cancer cells.

FIG. 10A-10D. C3 conditioned CSF by opening the blood-CSF-barrier. (A) Commercial dot-blot array was employed to measure proteins present in CSF of two patients without leptomeningeal metastasis, who later developed leptomeningeal metastasis. Analytes significantly upregulated are presented. (B) LLC-LeptoM cells instilled into the cisterna magna of C3aR wild-type ($^{+/+}$) or knock-out ($^{-/-}$) syngenic mice. Tumor growth was monitored by BLI. (C) ELISA for amphiregulin of CSF from suspected of leptomeningeal metastasis. Final clinical diagnosis is indicated. (D) Mice were parenterally pretreated with recombinant mouse C3 (purple) or vehicle (green) as described in FIG. 7E. Amphiregulin was measured by ELISA in CSF and plasma.

Figure 11A:
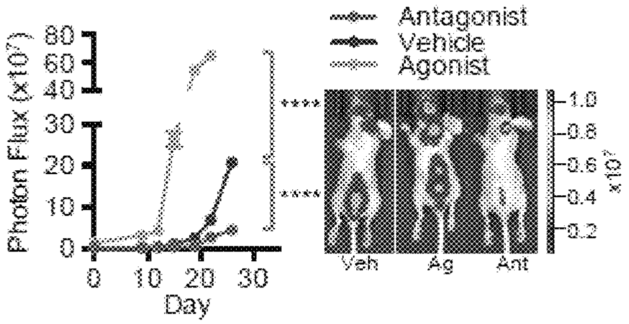
Figure 11B:
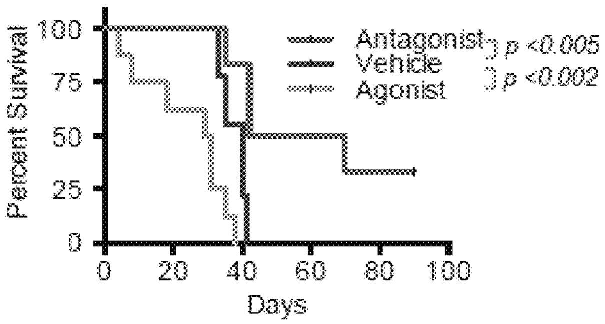
Figure 11C:
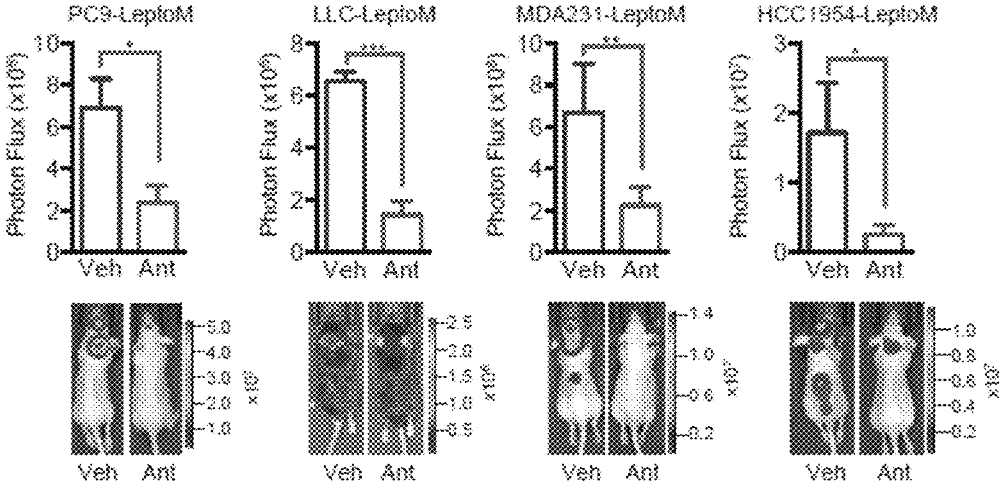

FIG. 11A-11C. C3aR as a therapeutic target in leptomeningeal metastasis. (A) 2,000 MDA231-LeptoM cells were introduced into the cisterna magna on day 0. Mice were treated with 10 mg/kg C3aR agonist (Ag), 10 mg/kg antagonist (Ant) or vehicle (Veh) I.P. twice weekly, tumor cell growth was monitored by BLI. n=10 mice per group. ****p<0.0001 (B) Survival analysis of mice treated in (A). (C) 2,000 MDA231-LeptoM, PC9-LeptoM, HCC1954-LeptoM or LCC-LeptoM cells were introduced into the CSF on day 0 and treated with Veh or Ant as described in (A). n=10 mice per group. BLI on day 14 is illustrated. *p<0.05; p<0.01; * p<0.001.

5. DETAILED DESCRIPTION OF THE INVENTION

For clarity of description, and not by way of limitation, the detailed description is divided into the following subsections:

(i) model of leptomeningeal metastatic disease;
(ii) Agonists of C3 or C3aR;
(iii) Antagonists of C3 or C3aR;
(iv) methods of using agonists of C3 or C3aR;
(v) methods of using antagonists of C3 or C3aR; and
(vi) diagnostic methods and associated treatments.

5.1 Model of Leptomeningeal Disease

In certain non-limiting embodiments, the present invention provides for a model system for leptomeningeal metastasis comprising a host animal inoculated with leptomeningeal metastatic cells ("LeptoM" cells), said LeptoM cells prepared by a method comprising inoculating a first generator animal with parental cancer cells and then, after a period of time, collecting cancer cells from the meninges of the first generator animal and inoculating said collected cells into a second generator animal and then, after a period of time, collecting cancer cells from the meninges of the second generator animal where said collected cells are "Int" cells, optionally repeating said selection step, and then systemically introducing Int cells into a host animal, whereby introduced cells that localize to the meninges of the host animal are "LeptoM" cells and may be collected and used to inoculate, systemically or into the subarachnoid space, one or more further host animals and thereby form leptomeningeal cancer cell growth in the subsequent host animal(s). After collection and before re-introduction, Int and LeptoM cells may optionally be expanded in culture and/or preserved for future use. In certain non-limiting embodiments, the phenotype of the cells may be selected during culture to produce an essentially homogeneous cell population. In certain non-limiting embodiments, a parental cell, an Int cell, and/or a LeptM cell may be engineered to contain and express, constitutively or inducibly, one or more detectable marker (i.e., introduced reporter construct), for example, but not limited to, GFP (or another fluorescent protein (27)) and/or luciferase.

In certain non-limiting embodiments, the present invention provides for a model system for leptomeningeal metastasis comprising a model animal inoculated with leptomeningeal metastatic cells prepared by a method comprising inoculating, into the subarachnoid space (e.g. into a cistern in the brain) of a first generator animal, parental cancer cells and then, after a period of time, collecting cancer cells from the meninges of the first generator animal and inoculating said collected cells into the subarachnoid space of a second generator animal, optionally repeating said selection step one or more times, to obtain a population of leptomeningeal metastatic "Int" cells. After collection and before re-introduction, Int cells may optionally be expanded in culture and/or preserved for future use. In certain non-limiting embodiments, the phenotype of the cells may be selected during culture to produce an essentially homogeneous cell population. In certain non-limiting embodiments, an Int cell may contain and express, constitutively or inducibly, one or more detectable marker, for example, but not limited to, GFP (or another fluorescent protein (27)) and/or luciferase. Said Int cell may then be introduced into a host animal as set forth above to generate LeptoM cells.

In various non-limiting embodiment, the present invention provides for a purified population of Int or LeptoM cells, optionally in preservative solution or culture medium. As set forth above, said cells may contain introduced genes encoding one or more detectable marker. In certain embodiments, the present invention provides for a kit containing said cells.

For example, but not by way of limitation, the model system may be prepared as follows. Cells of a cancer cell line, such as, but not limited to, a breast, lung, or melanoma cell line, optionally labeled with one or more detectable marker (e.g. a fluorescent and/or a bioluminescent marker, such as, but not limited to, green fluorescent protein and luciferase), may be inoculated into a first generator animal. As a specific, non-limiting example, 20,000 parental cells stably expressing GFP and luciferase may be injected into the cisterna magna of a mouse (17). Growth of the cells may then be monitored, for example, every second day by bioluminescent imaging, and the health of the mice may be regularly monitored. When leptomeningeal metastatic growth involves the entire CNS or when significant morbidity develops, the mice may be euthanized, the brain removed and the basilar meninges may be imaged to confirm the presence of cancer cells bearing detectable marker(s) (e.g., bioluminescence). Where cancer cells are present, the basilar meninges may then be rinsed with PBS to collect cells residing in this space. The collected cells may then be grown in culture, for example, until the majority or essentially all the cells present were those possessing a reporter construct (e.g., GFP). Once an essentially pure population has been obtained, the cultured cells may then be injected into the cisterna magna of a second generator mouse, allowed to grow and collected. In certain embodiments, at least three rounds of such selection are performed. The resulting cells are referred to herein as "Int" cells. The Int derivatives represent cells selected for capacity to survive within the leptomeninges. To form a model animal, an effective number of Int cells may be injected into the systemic circulation, for example, 50,000 Int cells may be injected intracardially into a host mouse, and allowed to form metastases. Cancer cells within the leptomeninges ("LeptoM") may then be collected as before. These cells, termed "LeptoM" represent hematogenously disseminated cancer cells that have successfully entered the leptomeninges from the systemic circulation and survived within the CSF (see FIG. 1).

5.2 Agonists of C3 or C3AR

An agonist of C3 or C3aR is an agent that increases or promotes the biological activity of C3 or C3a, including, but not limited to, its functionality in the complement system, its binding affinity for C3aR, and/or its activity as an anaphylotoxin.

One non-limiting example of a $C_3aR$ receptor agonist is compound C4494 from Sigma Chemicals, Benzeneacetamide, α-cyclohexyl-N-[1-[1-oxo-3-(3-pyridinyl)propyl]-4-piperidinyl]-, α-cyclohexyl-N-[1-[1-oxo-3-(3-pyridinyl) propyl]-4-piperidinyl]-benzeneacetamide, CAS Number 944997-60-8, $C_{27}H_{35}N_3O_2$ with the structure shown below.

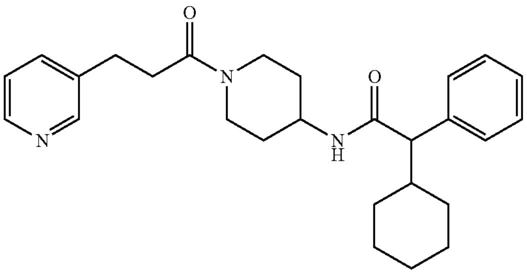 [SMILES: O=C(NC1CCN(C(=O)CCc2cccnc2)CC1)C(c1ccccc1)C1CCCCC1]

Other non-limiting examples of C3 and C3aR agonists that may be used include those described in Singh et al, 2015, Bioor. Med. Chem. Lett. 25:5604-5608, such as, but not limited to, compounds of Formula I:

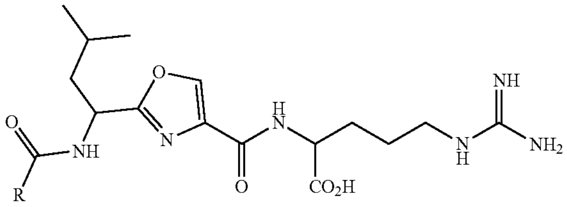

where R may be phenyl, substituted phenyl, aryl, heteroaryl, pyridine, or substituted pyridine, lower alkyl alkoxy, or

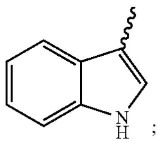

;

or compounds of Formula II:

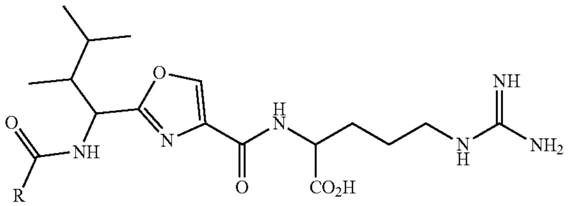

where R may be phenyl, substituted phenyl, aryl, heteroaryl, pyridine, or substituted pyridine, e.g.,

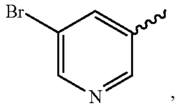

, or

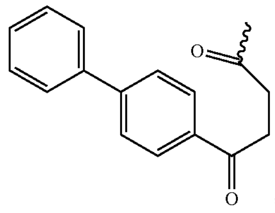

;

including, for example but not by limitation, compounds of Formula I or Formula II having a heterocyclic nitrogen separated from an amide carbonyl group by two carbons contained in an aromatic ring.

Other non-limiting examples of C3 and C3aR agonists that may be used include those described in Scully et al, 2010, J. Med. Chem. 53:4938-4948, such as, but not limited to, hexapeptides Phe-Ile-Pro-Leu-Ala-Arg, Phe-Trp-Pro-Leu-Ala-Arg; Trp-Trp-Thr-Leu-Ala-Arg; Phe-Tyr-Thr-Leu-Ala-Arg; Phe-Trp-Thr-Leu-Ala-Arg; Phe-Leu-Thr-Leu-Ala-Arg; Phe-Leu-Gly-Leu-Ala-Arg; and Phe-Leu-Thr-Leu-Ar.

In other non-limiting examples the agonist may be a peptide comprising the sequence Tyr-Pro-Leu-Pro-Arg, as described in Jinmaa et al., 2001, Peptides 22(1):25-32.

5.3 Antagonists of C3 or C3AR

An antagonist of C3 or C3aR is an agent that reduces or inhibits the biological activity of C3 or C3a, including, but not limited to, the functionality of C3 in the complement system and/or its activity as an anaphylotoxin.

One non-limiting example of a $C_3aR$ antagonist is SB 290157 (28), having the chemical name N2-[2-(2,2-diphenylethoxy)acetyl]-L-arginine, 2,2,2-trifluoroacetate, chemical formula $C_{22}H_{28}N_4O_4{\cdot}CF_3COOH$ and the following chemical structure:

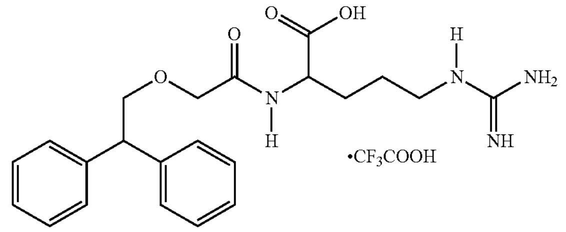 [SMILES: N=C(N)NCCCC(NC(=O)COCC(c1ccccc1)c1ccccc1)C(=O)O ; "·CF3COOH"]

Another non-limiting example of a $C_3$aR antagonist is SK&F 63649 (28) having the following structure:

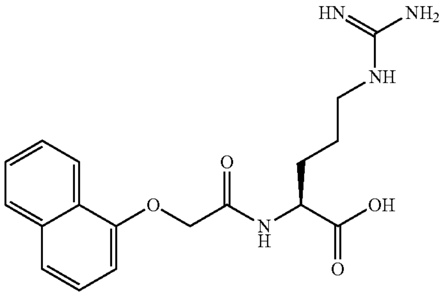 [SMILES: N=C(N)NCCC[C@H](NC(=O)COc1cccc2ccccc12)C(=O)O]

Other non-limiting examples of C3aR antagonists include compounds of Formula III below which inhibit C3a-induced calcium mobilization in RBL-2H3 cells (as described in ref 28) or an equivalent cell line with an IC50 between 5 and 75 nM:

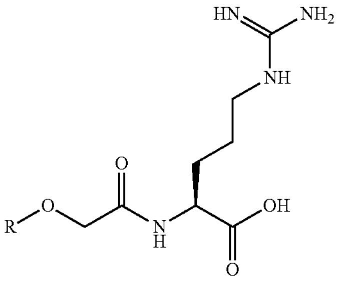

wherein the R attached to —O— may be aryl, heteroaryl, phenyl, diphenyl, diphenyl lower (C1-C4) alkyl, lower alkyl diphenyl, naphthyl, naphthyl lower alkyl, lower alkyl naphthyl, quinoline, quinoline lower alkyl, lower alkyl quinoline, purine, lower alkyl purine, purine lower alkyl, where any of the foregoing can be unsubstituted or substituted with lower alkyl, halogen, hydroxy or lower alkoxy.

Other non-limiting examples of C3 and C3aR antagonists that may be used include those described in Scully et al, 2010, J. Med. Chem. 53:4938-4948, such as, but not limited to, Phe-Leu-Thr-Cha-Ala-Arg.

5.4 Methods of Use of Agonists of C3 or C3AR

In certain non-limiting embodiments, the invention provides for a method of increasing permeability of the B-CSF-B in a subject in need of such treatment comprising administering, to the subject, an effective amount of an agonist of C3 or C3aR and optionally a second therapeutic agent, where treatment with the agonist increases the amount of second therapeutic agent in the CSF and thereby enhances its efficacy. The agonist and second therapeutic agent are administered to the subject in a manner such that the agonist may enhance the effectiveness of the second therapeutic agent, so that they may be administered, for example and not by way of limitation, together, or concurrently, or sequentially.

In certain non-limiting embodiments, the invention provides for a method of treating a subject having a disorder of the central nervous system, comprising administering, to the subject, an effective amount of (i) an agonist of C3 or C3aR and (ii) a second therapeutic agent, where treatment with the agonist increases the amount of second therapeutic agent in the CSF and thereby enhances its efficacy.

For example and not by way of limitation, the subject in need of such treatment may be suffering from an infectious disease of the central nervous system, including but not limited to a bacterial, viral, fungal, protozoan, or parasitic (e.g., hemlinthic) infection (wherein the second therapeutic agent may be, for example, an antimicrobial, antibacterial, antiviral, antifungal, antiprotozoal, antiparasitic, or antihelminthic agent) including but not limited to infective meningitis.

As another example, the subject may be suffering from a cancer/malignant disease of the central nervous system (wherein the second therapeutic agent may be an anticancer agent), including but not limited to breast cancer, lung cancer, melanoma, lymphoma, or glioblastoma, including but not limited to leptomeningeal meningitis.

As another example, the subject may be suffering from a degenerative disease of the nervous system, such as, but not limited to, Alzheimer's disease, Parkinson's Disease, Huntington's Chorea, or Pick's Disease (wherein the second therapeutic agent may be a treatment for that condition). As another example, the subject may be suffering from multiple sclerosis.

As other examples, the subject may be suffering from a cerebrovascular disease; and/or acute damage to the CNS, for example by cerebrovascular accident, surgery, or trauma, and the second therapeutic agent may be an agent that modulates coagulation, that modulates vasoconstriction, reactive oxygen species, etc.

In certain embodiments, the second therapeutic agent is a genetically modified cell. In certain embodiments, the second therapeutic agent is a small molecule; in other embodiments, it is a biologic.

The invention therefore may be used to improve access of systemically administered therapeutic agents to the CSF, meninges and CNS.

In non-limiting embodiments, the subject may be a human or non-human animal subject such as, but not limited to, a non-human primate, a mouse, a rat, a hamster, a rabbit, a guinea pig, a dog, a cat, a horse, a cow, a pig, or a sheep.

In non-limiting embodiments, a C3 or C3aR agonist may be administered to a subject by any route known in the art, including but not limited to, oral, intravenous, intraarterial, intrathecal, nasal, peritoneal, subcutaneous, intramuscular, rectal, etc.

In non-limiting embodiments, a C3 or C3aR agonist may be administered at a dose of between about 0.05 and 100 mg/kg, or between about 0.5 and 50 mg/kg, or between about 0.1 and 10 mg/kg or between about 0.5 and 2 mg/kg, or less than 0.5 mg/kg. In non-limiting embodiments, said dose may be administered once a day, twice a day, once a week, twice a week, once a month, twice a month, once every other month, or once every third month. In non-limiting embodiments, the period of treatment may be at least one day, at least one week, at least one month, at least two months, or at least three months.

5.5 Methods of Use of Antagonists of C3 or C3AR

In certain non-limiting embodiments, the present invention provides for a method of decreasing permeability of the B-CSF-B in a subject in need of such treatment comprising administering, to the subject, an effective inhibitory amount of an antagonist of C3 or C3aR (where "inhibitory" refers to decreased permeability of the B-CSF-B to certain substances in the blood (e.g., based on molecular weight, size, charge, degree of hydrophobicity, etc.) and/or to metastatic cancer cells).

In certain non-limiting embodiments, the present invention provides for a method of reducing the risk of leptomeningeal metastasis in a subject in need of such treatment, comprising administering, to the subject, an effective inhibitory amount of an antagonist of C3 or C3aR (where "inhibitory" refers to decreased permeability of the B-CSF-B to metastatic cancer cells).

For example, but not by way of limitation, the subject may be suffering from a malignant disease, and is at risk of cancer cells penetrating the B-CSF-B barrier; has findings that support a suspicion that the subject has leptomeningeal disease; or has findings that support a diagnosis of leptomeningeal disease; and/or said cancer is, for example but not limited to, breast cancer, lung cancer, or melanoma.

As another non-limiting example, the subject may have been exposed to an intrinsic or extrinsic toxin or infectious agent so that it is desirable to protect the central nervous system from being accessed by the infectious agent or toxin. For example, the present invention provides for a method of treating a subject suffering from a metabolic disease or a disease mediated by a toxin (e.g. botulism poisoning) or exposed to a toxin, comprising administering to the subject an effective inhibitory amount of an antagonist of C3 or C3aR. Said method of treatment may further comprise administering a second therapeutic agent directed at the infectious agent, metabolic disease or toxin.

In certain non-limiting embodiments, the present invention provides for a method of treating a subject having or suspected of having a cancer, comprising treating the subject with an effective amount of a C3 or C3aR antagonist and optionally a second therapeutic agent. For example, and not by way of limitation, said therapeutic agent may be a chemotherapy agent or an immunomodulatory agent.

In certain non-limiting embodiments, the invention provides for a method of treating a subject having or suspected of having a cancer, comprising alternately treating the subject with (i) a C3 or C3aR antagonist and (ii) a C3 or C3aR agonist and a second therapeutic agent. For example, it may be desirable to treat the subject with C3 and/or C3aR receptor antagonist for a period of time to protect the CNS from metastatic disease, but then administer a C3 or C3aR agonist and a second therapeutic agent to aid the second therapeutic agent to penetrate the B-CSF-B.

In certain non-limiting embodiments, the invention provides for a method of treating a subject having or suspected of having a cancer, comprising diagnosing leptomeningeal metastasis in a subject by determining that the level of C3 in the CSF of the subject is elevated relative to the level in the CSF of a healthy control subject and then treating the subject with a C3 or C3aR antagonist and/or a C3 or C3aR antagonist, optionally together with a second therapeutic agent.

In non-limiting embodiments, the subject may be a human or non-human animal subject such as, but not limited to, a non-human primate, a mouse, a rat, a hamster, a rabbit, a guinea pig, a dog, a cat, a horse, a cow, a pig, or a sheep.

In non-limiting embodiments, a C3 or C3aR antagonist may be administered to a subject by any route known in the art, including but not limited to, oral, intravenous, intraarterial, intrathecal, nasal, peritoneal, subcutaneous, intramuscular, rectal, etc.

In non-limiting embodiments, a C3 or C3aR antagonist may be administered at a dose of between about 0.05 and 100 mg/kg, or between about 0.5 and 50 mg/kg, or between about 0.1 and 10 mg/kg or between about 0.5 and 2 mg/kg, or less than 0.5 mg/kg. In non-limiting embodiments, said dose may be administered once a day, twice a day, once a week, twice a week, once a month, twice a month, once every other month, or once every third month. In non-limiting embodiments, the period of treatment may be at least one day, at least one week, at least one month, at least two months, or at least three months.

5.6 Diagnostic Methods and Associated Treatments

In certain non-limiting embodiments, the present invention provides for a method of diagnosing leptomeningeal metastasis in a subject, comprising determining that the level of C3 in the CSF of the subject is elevated relative to the level in the CSF of a healthy control subject.

In certain non-limiting embodiments, the present invention provides for a kit for practicing said method, said kit comprising a means for detecting C3 such as but not limited to an anti-C3 antibody or antibody fragment or single chain antibody, optionally: instructions or access to instructions for use of the kit and its use in determining C3 levels in the CSF and its association with leptomeningeal metastatic disease; a secondary antibody and/or detection agent; and/or materials for performing a lumbar puncture or CSF reservoir tap. Said kit may further comprise an antibody suitable for detecting a breast cancer, lung cancer, or melanoma cell in the CSF. Said kit may further comprise a means for determining the level of glucose in the CSF. Said kit may further comprise a positive and/or negative control sample for C3 present in CSF in the presence and/or absence of leptomeningeal disease.

6. EXAMPLE 1: GENE "SIGNATURE" OF LEPTOMENINGEAL METASTASIS

Leptomeningeal metastasis represents a rare but fatal outcome of disseminated cancer. To this end, we have created interrogable mouse models of breast and lung cancer that separate the molecular characteristics required for cancer cell access to the leptomeningeal space from those characteristics needed for cancer cell survival within the CSF. These models are both histologically and transcriptomally distinct from parenchymal metastases. Transcriptomal profiling of these diverse models representing breast and lung cancers in both xenograft and syngeneic systems has identified a distinct set of genes or "signature" differentially expressed by cells competent to seed and grow within the leptomeninges. This signature provides evidence that circulating cancer cells produce complement C3. C3 is detectable in CSF from patients with cytology- or MRI-proven leptomeningeal metastasis. This protein spontaneously hydrolyzes to C3a+C3b. Without being bound by any particular theory, we hypothesize that cancer-derived C3a binds to the G-protein coupled receptor, C3aR, on the choroid plexus, resulting in breakdown of the blood-CSF-barrier and entry of plasma contents into the CSF, and this conditions the leptomeningeal space to make the CSF a more hospitable environment for cancer cell growth. Accordingly, genetic or pharmacologic blockade of either C3 or C3aR may be used to inhibit growth of cancer cells within this space. Conversely, we have found that C3aR agonism disrupts the blood-CSF-barrier and increases its permeability. Manipulation of the C3-C3aR axis shows great promise as a therapeutic approach for both leptomeningeal metastasis and potentially infectious meningitis as well.

6.1 Mouse Modeling of Leptomeningeal Metastasis

Previous work in the Massagué lab has shown that mouse models represent a powerful tool for the study of metastatic cancer (8-13). In this approach, human or mouse malignant cell lines are selected in vivo for metastasis to specific target organs. First, cancer cell lines are hematogenously disseminated and allowed to form metastases. Then, metastatic tumors at the target site (for example, the brain) are collected. These cells are expanded in culture, and are re-inoculated into mice until a population is generated that reliably metastasizes to the target organ (14). Transcriptomal analysis comparing the parental cell line with the metastatic cell line allows for identification of organ-specific metastasis genes (12, 15, 16).

To adapt this system to leptomeningeal metastases, we faced two main roadblocks. First, multiple anatomic routes are proposed that may result in leptomeningeal seeding. Although hematogenous dissemination is the most likely route for breast and lung cancer to access the CSF space, it is not the only possible path to entry. Second, leptomeningeal metastasis is a rare clinical event (5-10%) in patients with cancer.

To overcome these obstacles, we began by selecting cancer cells within the leptomeningeal space prior to subsequent hematogenous dissemination (FIG. 1). As an initial step, parental cells stably expressing GFP and luciferase were injected into the cisterna magna of a mouse (17). Growth of the cells was monitored every second day by bioluminescent imaging, and the health of the mice was monitored daily. When leptomeningeal metastatic growth involved the entire CNS or when significant morbidity developed, the mice were euthanized, the brain removed and the basilar meninges were imaged by bioluminescence. The basilar meninges were then rinsed with PBS to collect cells residing in this space. The cells were grown in culture until the only cells present were those possessing the reporter construct (GFP). Once a pure population was obtained, these cells were then re-injected into the cisterna magna of a second mouse, allowed to grow and collected. Cells collected after three rounds of selection were designated "Int". The Int derivatives represent cells selected for capacity to survive within the leptomeninges. 50,000 Int cells were injected intracardially, and allowed to form metastases. Cancer cells within the leptomeninges were collected as before. These cells, termed "LeptoM" represent hematogenously disseminated cancer cells that have successfully entered the leptomeninges from the systemic circulation and survived within the CSF (FIG. 1).

To assay the efficiency of this in vivo selection process, the LeptoM cells were injected intracardially into one group of mice. A second group received parental cells and a third group received BrM cells (metastatic derivatives previously created by our lab which preferentially produce brain metastases, see FIG. 1) (12). Overall metastatic burden was monitored by BLI. Because leptomeningeal metastases and parenchymal metastases will both give bioluminescent signal in the head region, neuro-anatomic localization of metastases in these animals was assayed by histopathology.

Because breast cancer and non-small cell lung cancer (NSCLC) are the most common primary tumors resulting in leptomeningeal disease (2), we employed the above methodology to create both breast (i.e., MDA231 and HCC1954) and lung (i.e., Lewis Lung Carcinoma ("LLC") and PC9) cancer models of leptomeningeal metastasis (FIG. 3A). The salient features of this modeling system will be evident with examination of a representative model, MDA231 (FIG. 2A-C).

Initial intra-cisternal inoculation of cells displayed evidence of selection. As shown in FIG. 2B, there was an initial cell loss (as evidenced by diminished BLI signal on day 2), followed by cell growth. In addition, with each subsequent round of selection, the cells became more adept at surviving in the leptomeninges (FIG. 2A). After hematogenous dissemination of these pre-selected Int cells, the cells accessed the leptomeninges in 71% of the mice injected, as illustrated by the representative mouse featured in FIG. 2C.

Figure 3D:
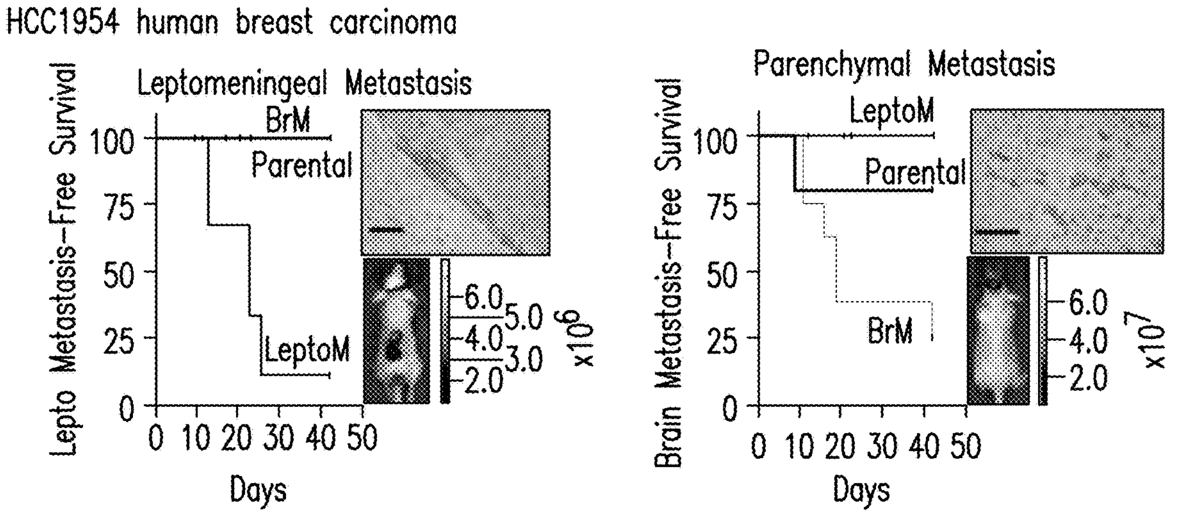
Figure 3E:
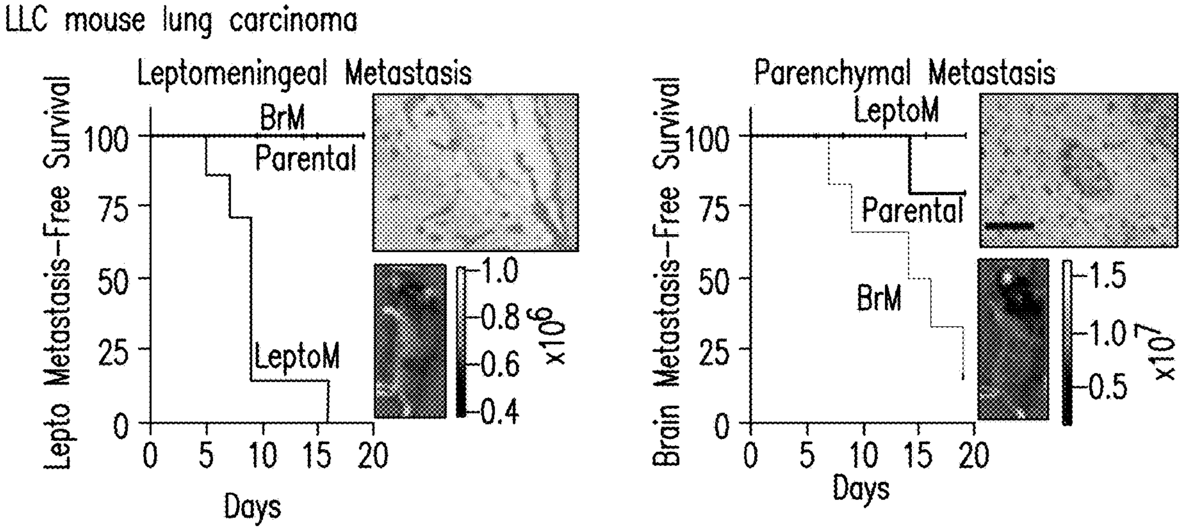

To assay the efficiency of in vivo selection, 20 mice were injected with either parental MDA231 (unselected) cells, MDA-BrM (parenchymal metastatic cells), or MDA-LeptoM cells (FIG. 3B). At the endpoint, leptomeningeal metastases were present in 86% of the mice injected with LeptoM cells; the cancer cells did not reach the leptomeningeal space in the BRM or parental cell lines. Conversely, the LeptoM cells did not generate parenchymal metastases. These data highlight two important features of this modeling system. First, the vast majority of in vivo selection occurs during the initial rounds of intracisternal inoculation, suggesting that survival within the leptomeninges represents a major barrier for cancer cells to overcome. Secondly, the traits required for propensity to generate parenchymal and leptomeningeal metastases can be selected independently (see FIGS. 3B-E), supporting the hypothesis that parenchymal and leptomeningeal metastases are biologically distinct entities. Importantly, these models displayed characteristic histopathologic features of leptomeningeal metastasis. Cancer cells layered over the pia mater of the cerebral hemispheres, coated the cerebellar folia, and filled and invaded the Virchow-Robin spaces.

6.2 Transcriptomal Analysis of Leptomeningeal Metastasis

The leptomeningeal microenvironment is substantially different than other sites of metastasis, including the neighboring brain parenchyma. The leptomeninges are filled with circulating cerebrospinal fluid (CSF), secreted by the choroid plexus. This biological fluid has a distinct composition, with notably lower protein, growth factors and glucose than either serum or tissue (18). Cancer cells adapted to thrive in such an environment are therefore likely to possess a distinct phenotype. Phenotypic changes might arise from either genetic or transcriptomal changes. However, previous exhaustive exome sequencing of mouse models created in the Massagué lab found little genetic divergence of metastatic derivative cell lines from the corresponding parental population. Thus, metastatic cell lines derived from parental cell lines primarily differ from one another in terms of their gene expression profile (19). We therefore hypothesized that the leptomeningeal derivatives would express a set of genes distinct from those expressed by cells metastatic to the brain parenchyma, or "BrM" cells (12, 16, 19).

To identify "leptomeningeal signature" genes, parental cell lines, and their corresponding leptomeningeal and brain parenchymal metastatic derivative cell lines (PAR, LeptoAS and BRM) cells, were grown in culture and total RNA was collected and mRNA was sequenced and analyzed (Prepease, Affymetrix, Santa Clara, CA). Genes differentially expressed in the same direction (up- or down-regulated) that are conserved between models of the same primary were collected. Genes upregulated within both the parenchymal (BrM) models and the leptomeningeal (LeptoM) models were excluded from the putative "leptomeningeal signature" list.

In collaboration with the MSK IGO Core Facility, RNASeq was performed as detailed above on PAR, BRM and LeptoM cells from four mouse models of leptomeningeal metastasis (FIG. 3A). Subsequent differential expression analysis was undertaken by the Bioinformatics core facility. Standard parameters for analysis were employed (Fold Change>2, Base mean>50, $p<0.05$). Principle component analysis reveals that the PAR, BrM and LeptoM cells have distinct expression profiles (FIG. 4). This is consistent with the hypothesis that leptomeningeal metastasis is biologically distinct from parenchymal brain metastases.

After applying the above parameters, including subtracting genes differentially expressed between parental and BrM models, there were 20 genes differentially expressed in all four models (FIG. 5A). Gene ontology analysis of this gene list revealed upregulation of the complement and coagulation cascade (FIG. 5B). Beyond upregulation of the pathway, the gene Complement C3 was upregulated in all models of leptomeningeal metastasis (FIG. 5C). This secreted protein is a key component of the complement cascade.

Figure 6A:
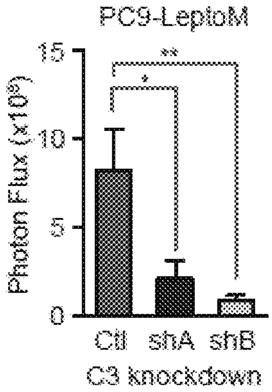
Figure 6B:
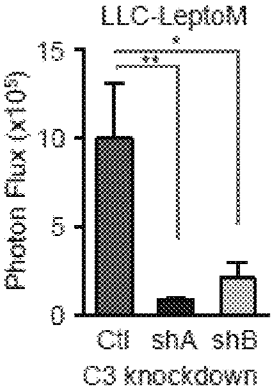
Figure 6C:
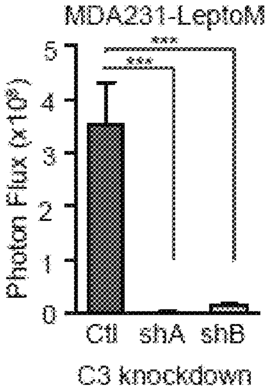
Figure 6D:
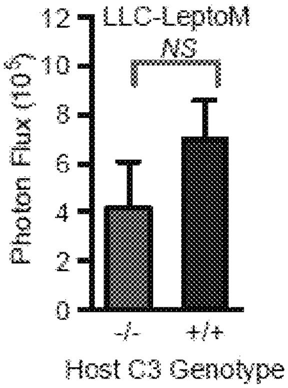

The importance of this gene in leptomeningeal metastasis was validated first in vivo. Two independent shRNA were employed to knock down C3 expression in LeptoM cells (FIG. 6A-C). These knockdown cells, or their control knockdown counterparts were inoculated into recipient mice and CNS bioluminescent signal was monitored. Near-complete knockdown of this gene in LeptoM cells led to a profoundly diminished propensity to develop leptomeningeal metastasis. Syngeneic C3 knockout mice hosted leptomeningeal metastasis equivalently to their wild type counterparts (FIG. 6D).

6.3 Manipulation of C3AR to Alter B-CSF-B Permeability

Preexisting C3aR antagonists and agonists were employed in a variety of in vitro, ex vivo and in vivo models to demonstrate the relevance of this signaling pathway in maintenance of B-CSF-B integrity.

The choroid plexus is composed of polarized epithelial cells, laminated to each other through tight junctions. These tight junctions comprise the blood-CSF-barrier. The underlying vascular endothelial cells are fenestrated, and allow free passage of macromolecules as well as some circulating cells.

The C3aR is a G protein-coupled receptor. It is present on a variety of cell types. Notably, it is present on renal tubule cells as well as certain lung cells. In both of these contexts, activation of the receptor leads to loosening of tight junctions and decreased barrier integrity function. In the renal tubule, this has been shown to lead to proteinuria; in the lung, this has been shown to lead to edema. Choroid plexus barrier function has been previously demonstrated to require PKC signaling (phorbol ester treatment lowers barrier function).

Figure 7A:
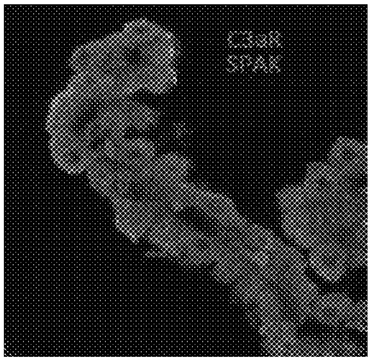
Figure 7B:
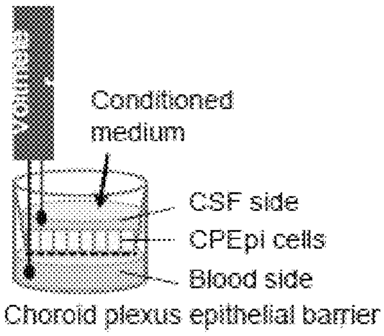
Figure 7C:
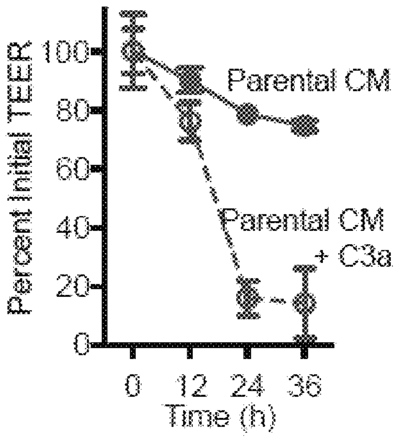
Figure 7D:
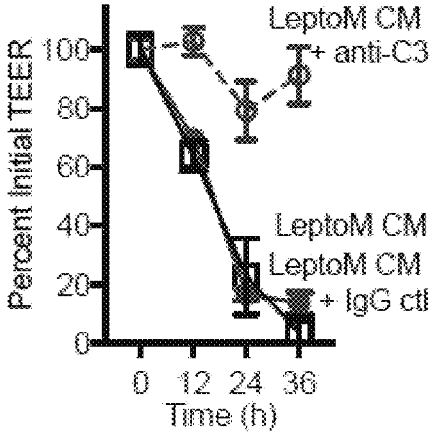

To address the hypothesis that C3aR might function similarly in the choroid plexus, we first established the presence of C3aR on choroid plexus epithelium (FIG. 7A). C3aR was not detectable on the cancer cells. Next, we examined the response of these cells to C3a in an in vitro model of the B-CSF (FIG. 7B). As previously demonstrated, HuCPEpithelial cells grow well on laminin-coated transwells, establishing tight junctions, and establish barrier function as measured by trans-epithelial electrical resistance (TEER) measurement. After addition of recombinant C3a, resistance across the monolayer was reduced (FIG. 7C); immunodepletion of C3a eliminated this effect (FIG. 7D). Thus, C3a activation increases the passage of ions across the barrier.

Figure 7E:
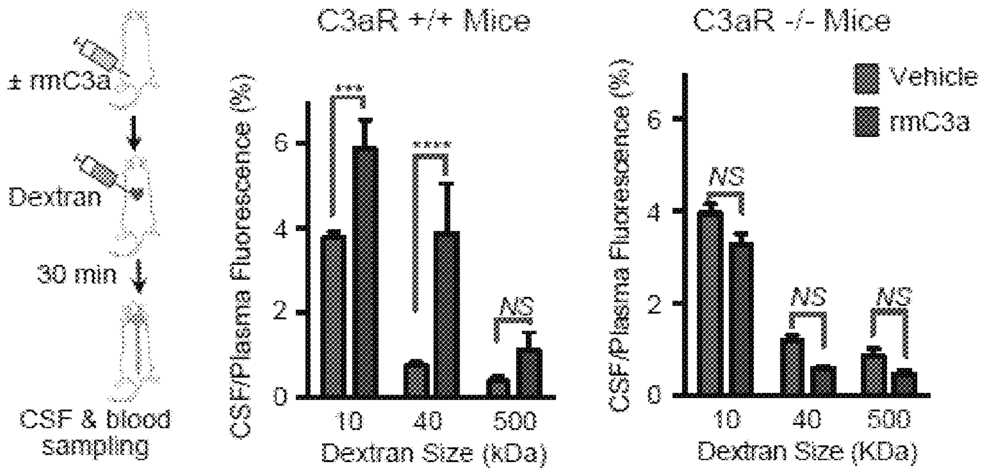
Figure 7F:
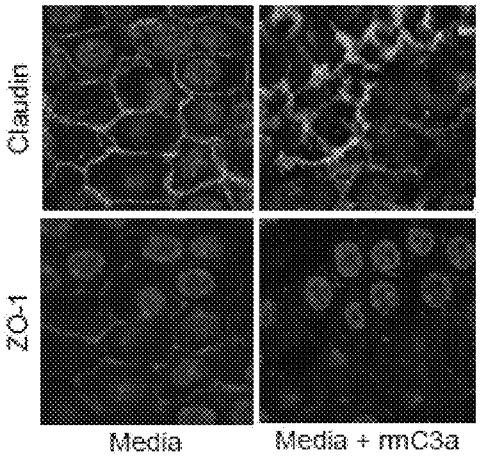

The passage of larger molecules was assessed through the use of fluorescently labeled Dextran passage in vivo. Mice, either wild type or knockout for C3aR were treated with C3aR agonist intraperitoneally prior to intracardiac injection of fluorescently derivatized 10, 40 and 500 kDa dextrans. Thirty minutes after this treatment, CSF was sampled by cisternal tap, and presence of the derivatized dextran was assayed by fluorescence. Passage of dextrans of 40 kDa and smaller from blood to CSF was increased after treatment with C3a in a C3aR-dependent manner (FIG. 7E). Treatment with recombinant C3a led to disorganization of tight junctions between choroid plexus epithelial cells, as measured by claudin immunofluorescence (FIG. 7F).

6.4 Validation and Model

Figure 8A:
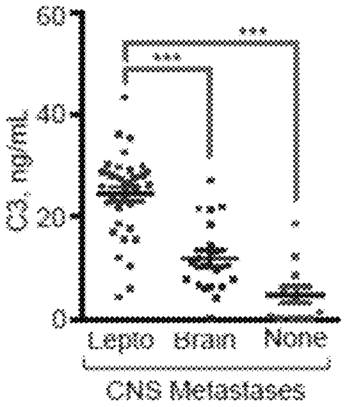
Figure 8B:
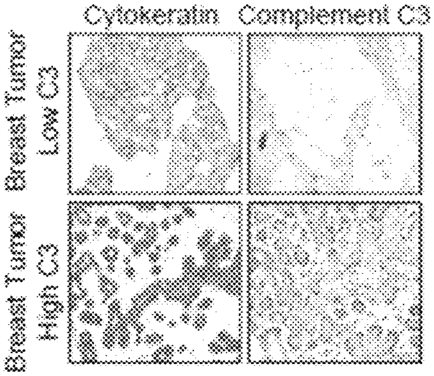
Figure 8C:
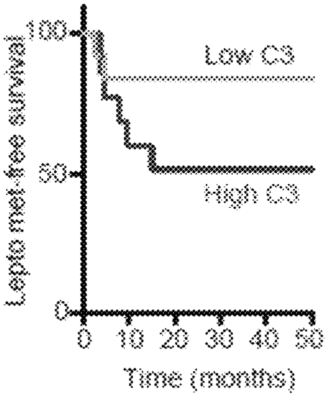
Figure 8D:
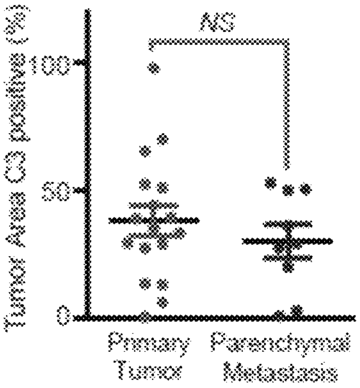
Figure 8E:
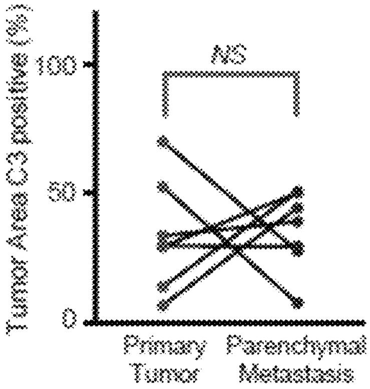

An increased level of C3 in human CSF was found to correlate with diagnosis of leptomeningeal metastasis (FIG. 8A). Primary tumors from patients suspected of harboring leptomeningeal metastases were stained with anti-C3 antibody, and patients were sorted into low C3-staining and high C3-staining categories (FIG. 8B). Clinical outcome of leptomeningeal metastasis correlated with elevated C3 expression in the primary tumor (FIG. 8C). In contrast, no correlation was uncovered between C3 expression in primary tumors of patients with parenchymal brain metastases (FIGS. 8D-E).

A schematic for the role of C3 in promoting leptomeningeal metastasis is shown in FIG. 9. Without being bound by any theory, complement C3 produced by cancer cells is thought to reduce the integrity of the B-CSF-B barrier, allowing for passage of plasma contents into the CSF and thereby creating a more hospitable environment for metastatic cancer cells. C3 generated by a cancer cell will be hydrolyzed into C3a and C3b. C3a will then bind to its cognate receptor, a GPCR on the choroid plexus epithelia. Activation of this receptor results in two distinct changes. First, signaling through PKC and MLCK leads to loosening of Claudin-based tight junctions. This allows for paracellular transport of plasma contents. Second, C3a receptor activation leads to upregulation of a variety of growth factors and chemokines. These too are released into the CSF. In this way, the cancer cell overcomes the choroid plexus barrier function, to supply itself with needed growth factors and metabolic intermediates. C3 and the $C_3$aR are at the center of this paracrine signaling pathway.

Figure 10A:
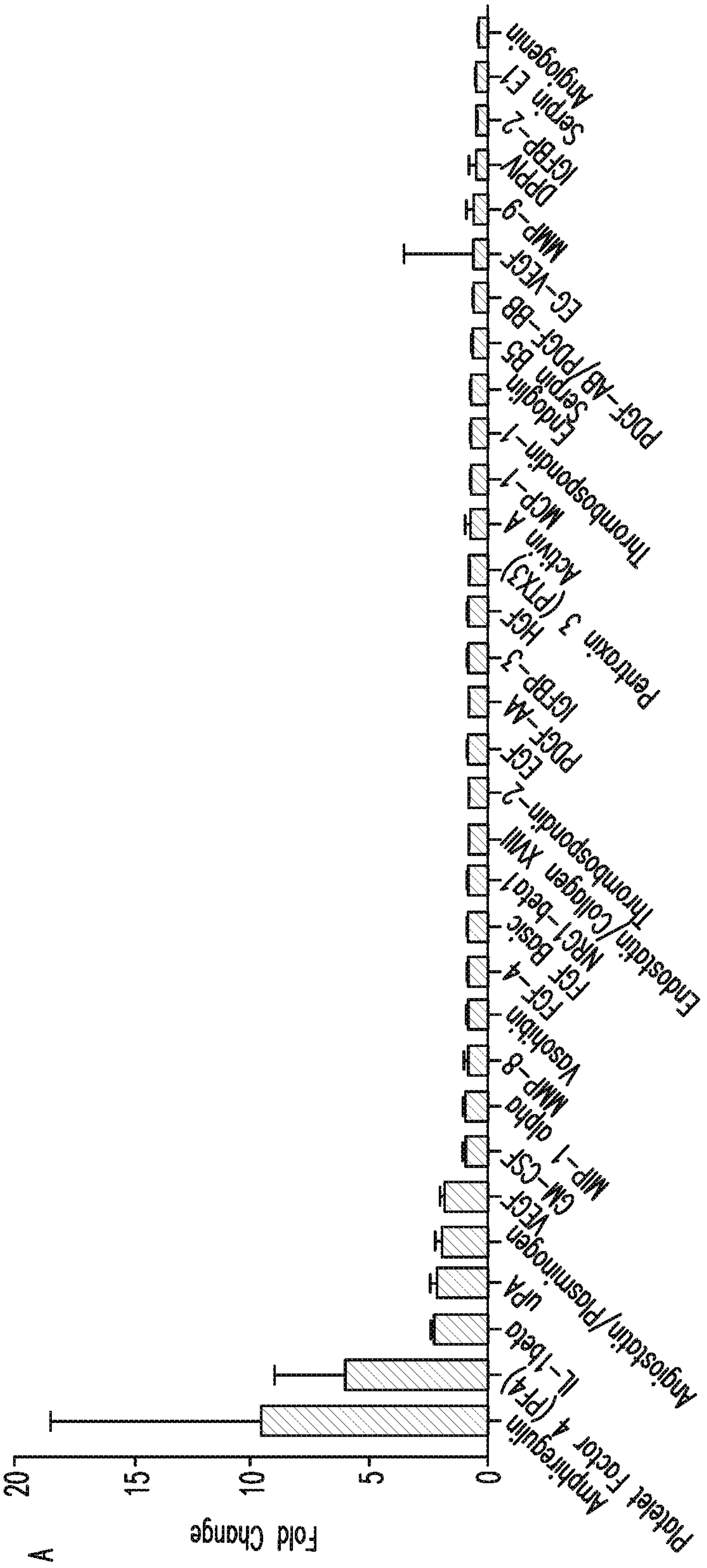
Figure 10B:
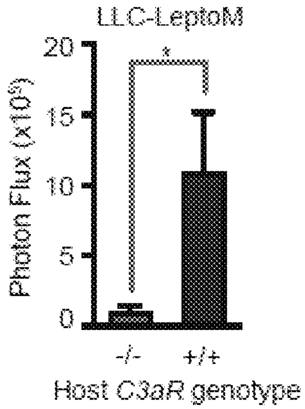
Figure 10C:
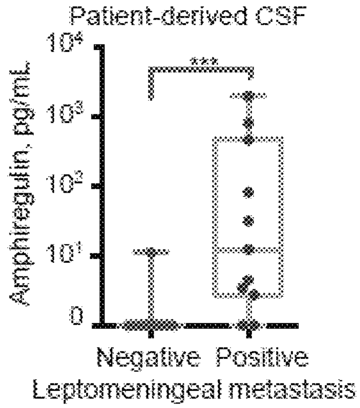
Figure 10D:
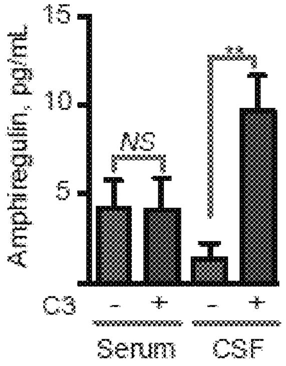

Leptomeningeal metastasis alters the composition of the CSF (FIG. 10A), including the growth factor amphiregulin (FIG. 10C). Cancer cell growth within the leptomeningeal space is improved in the presence of the C3aR in our models of leptomeningeal metastasis (FIG. 10B) after parenteral administration of C3a, serum amphiregulin is elevated within the CSF in mouse models.

7. EXAMPLE 2: EFFECTS OF MODULATION BY C3AR

In light of the cancer cell dependence on C3 for growth within the leptomeningeal space, as well as C3aR's importance in maintenance of CP barrier function, we elected to assay C3aR antagonist as well as agonists in models of leptomeningeal metastasis. First, 2,000 MDA LeptoM were injected into the cisterna magna of recipient mice. Next, treatment with either vehicle, C3aR agonist or antagonist was initiated. Tumor growth was followed with bioluminescent imaging FIG. 11A. As expected, tumor growth within the leptomeninges was slowed by treatment with C3aR antagonist, and accelerated with C3aR agonist treatment, and corresponded to a survival benefit for the mice treated with C3aR antagonist, FIG. 11B.

To expand these results beyond a single model, the antagonist treatment approach was tested in four models of leptomeningeal metastasis: MDA231, Hcc1954, PC9 and LLC. Cells corresponding to each of these models were inoculated into the leptomeningeal space of recipient mice on Day 0. Daily systemic treatment with C3aR antagonist SB290157 began on Day 1. Bioluminescent imaging to quantitate tumor cell growth is shown for each of the models, FIG. 11C. C3aR antagonist was associated with less leptomeningeal tumor growth for each model. These results support the use of C3aR antagonism as a method of treating leptomeningeal metastasis. In this approach, maintenance of B-CSF-B integrity inhibits cancer cell survival by inhibiting cancer cell access to plasma components, including protein, growth factors and metabolic intermediates.

Conversely, a major problem in treatment of leptomeningeal metastasis is gaining therapeutic access to the leptomeningeal space. This is true in other leptomeningeal pathologies, including infectious meningitis. In these scenarios, C3aR agonist treatment could be employed to open the B-CSF-B, rendering it permeable to systemic treatments, such as antibiotics, antivirals, antifungals or antiparasitic agents. In this way, C3aR agonism may be used to effectively expand the therapeutic repertoire for leptomeningeal pathologies.

8. REFERENCES

1. Leptomeningeal Metastases. DeAngelis, L M and J B Posner. Second ed. Oxford: Oxford University Press; 2009. p. 240-81.
2. Posner J B, Chernik N L. Intracranial metastases from systemic cancer. Advances in neurology. 1978; 19:579-92. PubMed PMID: 570349.
3. Le Rhun E, Taillibert S, Chamberlain M C. Carcinomatous meningitis: Leptomeningeal metastases in solid tumors. Surgical neurology international. 2013; 4(Suppl 4): S265-88. doi: 10.4103/2152-7806.111304. PubMed PMID: 23717798; PubMed Central PMCID: PMC3656567.
4. Altundag K, Bondy M L, Mirza N Q, Kau S W, Broglio K, Hortobagyi G N, Rivera E. Clinicopathologic characteristics and prognostic factors in 420 metastatic breast cancer patients with central nervous system metastasis. Cancer. 2007; 110(12):2640-7. doi: 10.1002/cncr.23088. PubMed PMID: 17960791.
5. Olson M E, Chernik N L, Posner J B. Infiltration of the leptomeninges by systemic cancer. A clinical and pathologic study. Archives of neurology. 1974; 30(2):122-37. PubMed PMID: 4405841.
6. Wasserstrom W R, Glass J P, Posner J B. Diagnosis and treatment of leptomeningeal metastases from solid tumors: experience with 90 patients. Cancer. 1982; 49(4): 759-72. PubMed PMID: 6895713.
7. Scott B J, Kesari S. Leptomeningeal metastases in breast cancer. American journal of cancer research. 2013; 3(2): 117-26. PubMed PMID: 23593536; PubMed Central PMCID: PMC3623833.
8. Kang Y, Siegel P M, Shu W, Drobnjak M, Kakonen S M, Cordon-Cardo C, Guise T A, Massague J. A multigenic program mediating breast cancer metastasis to bone. Cancer cell. 2003; 3(6):537-49. PubMed PMID: 12842083.
9. Kang Y, He W, Tulley S, Gupta G P, Serganova I, Chen C R, Manova-Todorova K, Blasberg R, Gerald W L, Massague J. Breast cancer bone metastasis mediated by the Smad tumor suppressor pathway. Proceedings of the National Academy of Sciences of the United States of America. 2005; 102(39):13909-14. doi: 10.1073/pnas.0506517102. PubMed PMID: 16172383; PubMed Central PMCID: PMC1236573.
10. Minn A J, Gupta G P, Siegel P M, Bos P D, Shu W, Giri D D, Viale A, Olshen A B, Gerald W L, Massague J. Genes that mediate breast cancer metastasis to lung. Nature. 2005; 436(7050):518-24. doi: 10.1038/nature03799. PubMed PMID: 16049480; PubMed Central PMCID: PMC1283098.
11. Chiang A C, Massague J. Molecular basis of metastasis. The New England journal of medicine. 2008; 359(26): 2814-23. doi: 10.1056/NEJMra0805239. PubMed PMID: 19109576.
12. Bos P D, Zhang X H, Nadal C, Shu W, Gomis R R, Nguyen D X, Minn A J, van de Vijver M J, Gerald W L, Foekens J A, Massague J. Genes that mediate breast cancer metastasis to the brain. Nature. 2009; 459(7249): 1005-9. doi: 10.1038/nature08021. PubMed PMID: 19421193; PubMed Central PMCID: PMC2698953.
13. Valiente M, Obenauf A C, Jin X, Chen Q, Zhang X H, Lee D J, Chaft J E, Kris M G, Huse J T, Brogi E, Massague J. Serpins promote cancer cell survival and vascular co-option in brain metastasis. Cell. 2014; 156 (5):1002-16. doi: 10.1016/j.cell.2014.01.040. PubMed PMID: 24581498; PubMed Central PMCID: PMC3988473.
14. Fidler I J. Selection of successive tumour lines for metastasis. Nature: New biology. 1973; 242(118):148-9. PubMed PMID: 4512654.
15. Zhang C, Zhang F, Tsan R, Fidler I J. Transforming growth factor-beta2 is a molecular determinant for site-specific melanoma metastasis in the brain. Cancer research. 2009; 69(3):828-35. doi: 10.1158/0008-5472.CAN-08-2588. PubMed PMID: 19141644; PubMed Central PMCID: PMC2633423.
16. Minn A J, Kang Y, Serganova I, Gupta G P, Giri D D, Doubrovin M, Ponomarev V, Gerald W L, Blasberg R, Massague J. Distinct organ-specific metastatic potential of individual breast cancer cells and primary tumors. The Journal of clinical investigation. 2005; 115(1):44-55. doi: 10.1172/JCI22320. PubMed PMID: 15630443; PubMed Central PMCID: PMC539194.
17. Reijneveld J C, Taphoorn M J, Voest E E. A simple mouse model for leptomeningeal metastases and repeated intrathecal therapy. Journal of neuro-oncology. 1999; 42(2):137-42. PubMed PMID: 10421071.
18. Spector R, Robert Snodgrass S, Johanson C E. A balanced view of the cerebrospinal fluid composition and functions: Focus on adult humans. Experimental neurology. 2015; 273:57-68. doi: 10.1016/j.expneurol.2015.07.027. PubMed PMID: 26247808.

19. Jacob L S, Vanharanta S, Obenauf A C, Pirun M, Viale A, Socci N D, Massague J. Metastatic Competence Can Emerge with Selection of Preexisting Oncogenic Alleles without a Need of New Mutations. Cancer research. 2015; 75(18):3713-9. doi: 10.1158/0008-5472. CAN-15-0562. PubMed PMID: 26208905; PubMed Central PMCID: PMC4573898.
20. Kesari S and Batchelor T T. Leptomeningeal metastases. Neurol. Clin. 2003; 21(1):25-66. PubMed PMID: 12690644.
21. DeAngelis L M and Boutras D. Leptomeningeal metastasis. Cancer Invest. 2005; 23(2):145-154. Pubmed PMID: 15813508.
22. Waki F et al. Prognostic factors and clinical outcomes in patients with leptomeningeal metastasis from solid tumors. J. Neurooncol. 2009; 93(2):205-212. Pubmed PMID: 19043775.
23. Brower J V et al. Management of leptomeningeal metastases: Prognostic factors and associated outcomes. J. Clin. Neurosci. 2016; 27:130-137. Pubmed PMID: 26778048.
24. Massague J and Obenauf A C. Metastatic colonization by circulating tumor cells. Nature. 2016; 529(7586):298-306. Pubmed PMID: 26791720.
25. Clarke J L et al. Leptomeningeal metastases in the MRI era. Neurology. 2010; 74(18):1449-1454. Pubmed PMID: 20439847.
26. Quail D F and Joyce J A. Microenvironmental regulation of tumor progression and metastasis. Nat. Med. 2013; 19(11):1423-1437.
27. Day R and Davidson M. The fluorescent protein palette: tools for cellular imaging. Chem. Soc. Rev. 2009; 38(10): 2887-2921.
28. Ames R S et al. Identification of a Selective Nonpeptide Antagonist of the Anaphyloxin C3a Receptor That Demonstrates Antiinflammatory Activity in Animal Models. J. Immunol. 2001; 166:6341-6348.
29. Rynkowski M A et al., C3a receptor antagonist attenuates brain injury after intracerebral hemorrhage. J Cerebral Blood Flow Metabolism. 2008; doi:10.1038/jcbfm.2008.95.

Various references are cited herein, the contents of which are hereby incorporated by reference in their entireties.

The invention claimed is:

1. A method of treating a subject suffering from a disorder of the central nervous system, comprising administering (i) an effective amount of an agonist of C3 or C3aR and (ii) an effective amount of a second therapeutic agent, wherein the second therapeutic agent is selected from the group consisting of an antimicrobial agent, an antibacterial agent, an antiviral agent, an antifungal agent, an antiprotozoal agent, an antiparasitic agent, an anthelmintic agent and an anticancer agent.

2. The method of claim 1, wherein the subject is suffering from an infectious disease.

3. The method of claim 2, wherein the infectious disease is infective meningitis.

4. The method of claim 1, wherein the subject is suffering from a cancer.

5. The method of claim 1, wherein the subject is suffering from a degenerative disorder.

6. The method of claim 1, wherein the agonist is an agonist of C3.

7. The method of claim 1, wherein the agonist is an agonist of C3aR.

8. The method of claim 1, wherein the agonist of C3aR is selected from the group consisting of compound C4494, Benzeneacetamide, a-cyclohexyl-N-[1-[1-oxo-3-(3-pyridinyl) propyl]-4-piperidinyl]-, a-cyclohexyl-N-[1-[1-oxo-3-(3-pyridinyl) propyl]-4-piperidinyl]-benzeneacetamide, CAS Number 944997-60-8, and

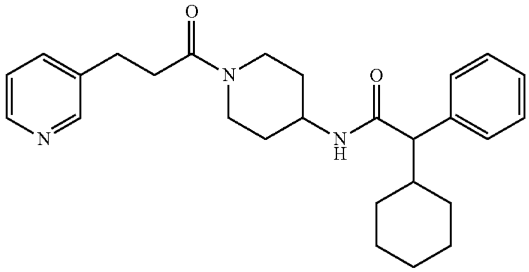

.

9. The method of claim 1, wherein the agonist of C3 or C3aR has formula

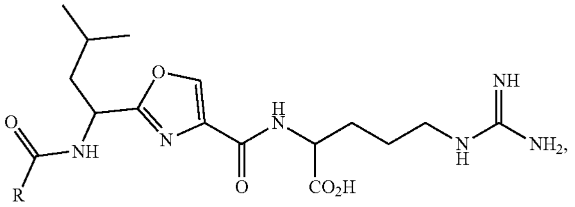

wherein R is selected from the group consisting of phenyl, substituted phenyl, aryl, heteroaryl, pyridine, or substituted pyridine, lower alkyl alkoxy, and

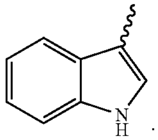

.

10. The method of claim 1, wherein the agonist of C3 or C3aR has formula

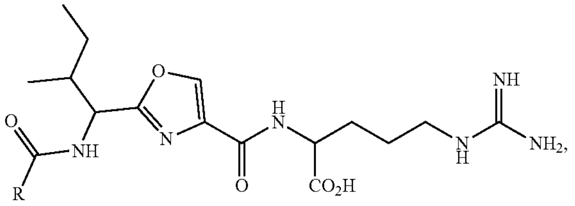

wherein R is selected from the group consisting of phenyl, substituted phenyl, aryl, heteroaryl, pyridine, substituted pyridine,

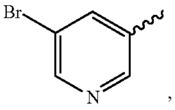, and 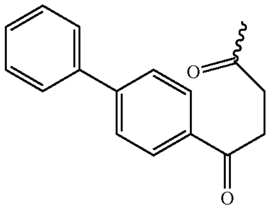.

11. The method of claim 1, wherein the agonist of C3 or C3aR is selected from the group consisting of Phe-Ile-Pro-Leu-Ala-Arg, Phe-Trp-Pro-Leu-Ala-Arg, Trp-Trp-Thr-Leu-Ala-Arg, Phe-Tyr-Thr-Leu-Ala-Arg, Phe-Trp-Thr-Leu-Ala-Arg, Phe-Leu-Thr-Leu-Ala-Arg, Phe-Leu-Gly-Leu-Ala-Arg, and Phe-Leu-Thr-Leu-Arg, and Tyr-Pro-Leu-Pro-Arg.

12. The method of claim 1, wherein the second therapeutic agent is selected from the group consisting of an antimicrobial agent, an antibacterial agent, an antiviral agent, an antifungal agent, an antiprotozoal agent, an antiparasitic agent, and an anthelmintic agent.

13. The method of claim 1, wherein the second therapeutic agent is an anticancer agent.

14. A method of treating a subject suffering from a disorder of the central nervous system, consisting of administering (i) an effective amount of an agonist of C3 or C3aR and (ii) an effective amount of a second therapeutic agent, wherein the second therapeutic agent is selected from the group consisting of an antimicrobial agent, an antibacterial agent, an antiviral agent, an antifungal agent, an antiprotozoal agent, an antiparasitic agent, an anthelmintic agent and an anticancer agent.

15. The method of claim 14, wherein the subject is suffering from an infectious disease.

16. The method of claim 15, wherein the infectious disease is infective meningitis.

17. The method of claim 14, wherein the subject is suffering from a cancer.

18. The method of claim 14, wherein the subject is suffering from a degenerative disorder.

19. The method of claim 14, wherein the agonist of C3 or C3aR is selected from the group consisting of compound C4494, Benzeneacetamide, a-cyclohexyl-N-[1-[1-oxo-3-(3-pyridinyl) propyl]-4-piperidinyl]-, a-cyclohexyl-N-[1-[1-oxo-3-(3-pyridinyl) propyl]-4-piperidinyl]-benzeneacetamide, CAS Number 944997-60-8,

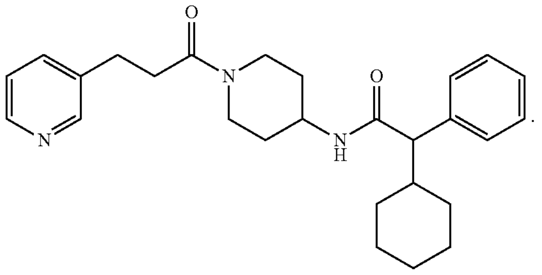 [SMILES: O=C(NC1CCN(C(=O)CCc2cccnc2)CC1)C(c1ccccc1)C1CCCCC1].

20. The method of claim 14, wherein the agonist of C3 or C3aR:

a) has formula

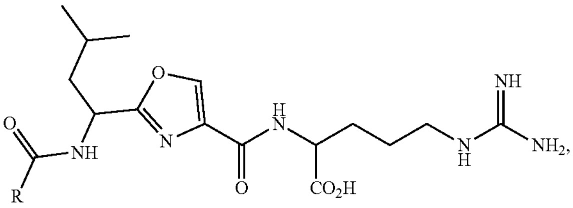, wherein R is selected from the group consisting of phenyl, substituted phenyl, aryl, heteroaryl, pyridine, or substituted pyridine, lower alkyl alkoxy, and

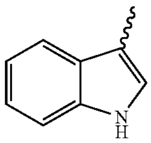;

or b) has formula

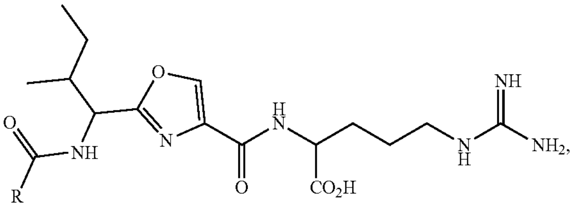, wherein R is selected from the group consisting of phenyl, substituted phenyl, aryl, heteroaryl, pyridine, substituted pyridine,

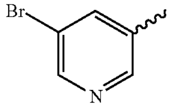, and 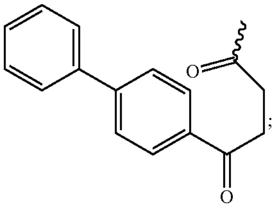;

or c) is Phe-Ile-Pro-Leu-Ala-Arg, Phe-Trp-Pro-Leu-Ala-Arg, Trp-Trp-Thr-Leu-Ala-Arg, Phe-Tyr-Thr-Leu-Ala-Arg, Phe-Trp-Thr-Leu-Ala-Arg, Phe-Leu-Thr-Leu-Ala-Arg, Phe-Leu-Gly-Leu-Ala-Arg, and Phe-Leu-Thr-Leu-Arg, and Tyr-Pro-Leu-Pro-Arg.

* * * * *